(12) United States Patent
Berthelot et al.

(10) Patent No.: US 9,139,862 B2
(45) Date of Patent: Sep. 22, 2015

(54) FLUORESCENT CYCLIC PEPTIDES, PREPARATION METHOD THEREOF AND USE OF THESE PEPTIDES FOR MEASURING THE ENZYMATIC ACTIVITY OF A PROTEASE ENZYME

(75) Inventors: Thomas Berthelot, Les Ulis (FR); Gérard Deleris, Bordeaux (FR)

(73) Assignees: COMMISSARIAT A L'ENERGIE ATOMIQUE ET AUX ENERGIES ALTERNATIVES, Paris (FR); UNIVERSITE VICTOR SEGALEN-BORDEAUX 2, Bourdeaux (FR)

( * ) Notice: Subject to any disclaimer, the term of this patent is extended or adjusted under 35 U.S.C. 154(b) by 892 days.

(21) Appl. No.: 12/737,082

(22) PCT Filed: Jun. 10, 2009

(86) PCT No.: PCT/EP2009/057194
§ 371 (c)(1),
(2), (4) Date: Apr. 22, 2011

(87) PCT Pub. No.: WO2010/000591
PCT Pub. Date: Jan. 7, 2010

(65) Prior Publication Data
US 2011/0256567 A1 Oct. 20, 2011

(30) Foreign Application Priority Data
Jun. 10, 2008 (FR) ..................... 08 53850

(51) Int. Cl.
*C07K 7/50* (2006.01)
*C12Q 1/37* (2006.01)
*C07K 7/64* (2006.01)

(52) U.S. Cl.
CPC ... *C12Q 1/37* (2013.01); *C07K 7/64* (2013.01); *G01N 2333/95* (2013.01); *G01N 2333/96494* (2013.01)

(58) Field of Classification Search
None
See application file for complete search history.

(56) References Cited

FOREIGN PATENT DOCUMENTS

WO WO 02/055098 7/2002

OTHER PUBLICATIONS

Moustoifa et al, Novel cyclopeptides for the design of MMP directed delivery devices: a novel smart delivery paradigm. Pharm Res. Aug. 2010;27(8):1713-21. doi: 10.1007/s11095-010-0164-0. Epub May 8, 2010.*
International Search Report for PCT/EP2009/057194 mailed Mar. 23, 2010 with English translation.
Benito et al., "Bicyclic Organo-Peptides as Selective Carbohydrate Receptors: Design, Solid-phase Synthesis, and on-bead Binding Capability", QSAR and Combinatorial Science, vol. 23, No. 2-3, Apr. 2004, pp. 117-129.
Berthelot et al., "Synthesis of Nε—(7-diethylaminocoumarin-3-carboxyl)- and Nε—(7-methoxycoumarin-3-carboxyl)-L-Fmoc lysine as tools for protease cleavage detection by fluorescence". Journal of Peptide Science, vol. 11, No. 3, Mar. 1, 2005, pp. 153-160.
Gruenewald et al., "Fluorescence Resonance Energy Transfer as a Probe of Peptide Cyclization Catalyzed by Nonribosomal Thioesterase Domains", Chemistry & Biology, vol. 12, No. 8, Aug. 2005, pp. 873-881.
Kelly et al., "Detection of Invasive Colon Cancer Using a Novel, Targeted, Library-Derived Fluorescent Peptide", Cancer Research, vol. 64, No. 17, Sep. 1, 2004, pp. 6247-6251.
Nagase et al., "Human Matrix Metalloproteinase Specificity Studies Using Collagen Sequence-Based Synthetic Peptides", Biopolymers, vol. 40, No. 4, Jan. 1, 1996, pp. 399-416.
Van Den Elsen et al, "On the Interaction between a Bactericidal Antibody and PorA Epitope of *Neisseria meningitidis* in Outer Membrane Vesicles: A Competitive Fluorescence Polarization Immunoassy", Analytical Biochemistry, vol. 247, No. 2, May 1, 1997, pp. 382-388.

* cited by examiner

*Primary Examiner* — Sheridan Swope
(74) *Attorney, Agent, or Firm* — Miles & Stockbridge P.C.

(57) ABSTRACT

The invention pertains to a cyclic peptide comprising the following sequence:

$$-S_1-X_1-S_2-X_2-$$

wherein $S_1$ is a first target peptide sequence of a protease enzyme $E_1$, $S_2$ is a second target peptide sequence of a protease enzyme $E_2$, $S_1$ and $S_2$ possibly being the same or different, said first peptide sequence $S_1$ and said second peptide sequence $S_2$ comprising 4 to 14 amino acids, $E_1$ and $E_2$ possibly corresponding to the same protease enzyme or to two different protease enzymes, $X_1$ is a probe carrying a fluorescent donor group and $X_2$ is a probe carrying a fluorescent or non-fluorescent acceptor group.
Application of these peptides to determination of the activity of protease enzymes.

12 Claims, 1 Drawing Sheet

SEQUENCE LISTING

```
<160> NUMBER OF SEQ ID NOS: 61

<210> SEQ ID NO 1
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 1

Gly Pro Gln Gly Leu Leu Gly Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 2

Ala Pro Gln Gly Ile Ala Gly Gln
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 3

Gly Pro Gln Gly Leu Ala Gly Gln
1               5

<210> SEQ ID NO 4
<211> LENGTH: 8
<212> TYPE: PRT
<213> ORGANISM: Artificial Sequence
<220> FEATURE:
```

<223> OTHER INFORMATION: Synthetic target peptide sequence of MMP

<400> SEQUENCE: 4

Gly Pro Leu Gly Ile Ala Gly Ile
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 5

Gly Pro Glu Gly Leu Arg Val Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 6

Tyr Glu Ala Gly Leu Gly Val Val
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 7

Ala Gly Leu Gly Val Val Glu Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 8

Ala Gly Leu Gly Ile Ser Ser Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 9

Gly Ala Met Phe Leu Glu Ala Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic target peptide sequence of MMP

```
<400> SEQUENCE: 10

Ile Pro Glu Asn Phe Phe Gly Val
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 11

Thr Glu Gly Glu Ala Arg Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 12

Arg Ala Ile His Ile Gln Ala Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 13

Leu Arg Ala Tyr Leu Leu Pro Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 14

Gly Pro Leu Gly Met Arg Gly Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 15

Pro Gln Gly Leu Glu Ala Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic target peptide sequence of MMP
<220> FEATURE:
```

```
<221> NAME/KEY: MISC_FEATURE
<222> LOCATION: (7)..(7)
<223> OTHER INFORMATION: Xaa is D-Arg

<400> SEQUENCE: 16

Pro Leu Gly Leu Trp Ala Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 17

Pro Leu Ala Leu Trp Ala Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (2)..(2)
<223> OTHER INFORMATION: Xaa is 3-cyclohexylalanine (Cha)
<220> FEATURE:
<221> NAME/KEY: MISC_FEATURE
<222> LOCATION: (3)..(3)
<223> OTHER INFORMATION: Xaa is alpha-aminobutyric acid (Abu)
<220> FEATURE:
<221> NAME/KEY: MISC_FEATURE
<222> LOCATION: (4)..(4)
<223> OTHER INFORMATION: Xaa is Cys(Me)

<400> SEQUENCE: 18

Pro Xaa Xaa Xaa His Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (2)..(2)
<223> OTHER INFORMATION: Xaa is 3-cyclohexylalanine (Cha)
<220> FEATURE:
<221> NAME/KEY: MISC_FEATURE
<222> LOCATION: (4)..(4)
<223> OTHER INFORMATION: Xaa is Cys(Me)

<400> SEQUENCE: 19

Pro Xaa Gly Xaa His Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (2)..(2)
<223> OTHER INFORMATION: Xaa is 3-cyclohexylalanine (Cha)
```

```
<220> FEATURE:
<221> NAME/KEY: MISC_FEATURE
<222> LOCATION: (4)..(4)
<223> OTHER INFORMATION: Xaa is Cys(Me)

<400> SEQUENCE: 20

Pro Xaa Gly Xaa His Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (5)..(5)
<223> OTHER INFORMATION: Xaa is N-3(2,4-dinitrophenyl)-L-2,3-
      diaminopropionyl (Dpa)

<400> SEQUENCE: 21

Pro Leu Gly Leu Xaa Ala Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: BINDING
<222> LOCATION: (3)..(4)
<223> OTHER INFORMATION: The third and fourth amino acids are separated
      by-(2-mercapto-4-methyl-pentanoyl)-

<400> SEQUENCE: 22

Pro Leu Gly Leu Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (4)..(4)
<223> OTHER INFORMATION: Xaa is Cys(Me)
<220> FEATURE:
<221> NAME/KEY: MISC_FEATURE
<222> LOCATION: (7)..(7)
<223> OTHER INFORMATION: Xaa is D-Arg

<400> SEQUENCE: 23

Pro Leu Gly Xaa His Ala Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 24

Arg Pro Leu Ala Leu Trp Arg
1               5
```

<210> SEQ ID NO 25
<211> LENGTH: 6
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (2)..(2)
<223> OTHER INFORMATION: Xaa is 3-cyclohexylalanine (Cha)
<220> FEATURE:
<221> NAME/KEY: MISC_FEATURE
<222> LOCATION: (4)..(4)
<223> OTHER INFORMATION: Xaa is Nor-valine (Nva)

<400> SEQUENCE: 25

Pro Xaa Gly Xaa His Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (7)..(7)
<223> OTHER INFORMATION: Xaa is Nor-valine (Nva)

<400> SEQUENCE: 26

Arg Pro Lys Pro Tyr Ala Xaa Trp Met
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 27

Pro Pro Gly Ala Tyr His Gly Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 28

Gly Pro His Leu Leu Val Glu Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 29

Pro Gln Gly Leu Glu Ala Lys
1               5

```
<210> SEQ ID NO 30
<211> LENGTH: 7
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (4)..(4)
<223> OTHER INFORMATION: Xaa is Nor-valine (Nva)
<220> FEATURE:
<221> NAME/KEY: MISC_FEATURE
<222> LOCATION: (5)..(5)
<223> OTHER INFORMATION: Xaa is N-3(2,4-dinitrophenyl)-L-2,3-
      diaminopropionyl (Dpa)

<400> SEQUENCE: 30

Pro Leu Ala Xaa Xaa Ala Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 31

Pro Leu Gly Met Trp Ser Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: BINDING
<222> LOCATION: (3)..(4)
<223> OTHER INFORMATION: The third and fourth amino acids are separated
      by-SCH[CH2CH(CH3)2]-CO-

<400> SEQUENCE: 32

Pro Leu Gly Leu Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 33

Arg Pro Pro Gly Phe Ser Ala Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 34

Arg Val Gly Phe Tyr Glu Ser Asp
1               5
```

```
<210> SEQ ID NO 35
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 35

Leu Leu Ser Ala Leu Val Glu Thr
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 36

Glu Ala Ile Pro Met Ser Ile Pro
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 37

Ile Ala Gly Arg Ser Leu Asn Pro
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 38

Lys Pro Gln Gln Phe Phe Gly Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 39

Asp Val Ala Gln Phe Val Leu Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 40

Asp Thr Leu Glu Val Met Arg Lys
1               5

<210> SEQ ID NO 41
```

```
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 41

Asp Val Gly His Phe Arg Thr Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 42

Asp Ser Gly Gly Phe Met Leu Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 43

Arg Val Ala Glu Met Arg Gly Glu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 44

Asp Leu Gly Arg Phe Gln Thr Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 45

Pro Phe Ser Pro Leu Val Ala Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 46

Ala Pro Gly Asn Ala Ser Glu Ser
1               5

<210> SEQ ID NO 47
<211> LENGTH: 8
```

-continued

```
<212> TYPE: PRT
<213> ORGANISM: Artificial Sequence
<220> FEATURE:
<223> OTHER INFORMATION: Synthetic target peptide sequence of MMP

<400> SEQUENCE: 47

Phe Ser Ser Glu Ser Lys Arg Glu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 48

Pro Pro Glu Glu Leu Lys Phe Gln
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 49

Gly Pro Leu Gly Met Arg Gly Leu
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (7)..(7)
<223> OTHER INFORMATION: Xaa is Nor-valine (Nva)

<400> SEQUENCE: 50

Arg Pro Lys Pro Val Glu Xaa Trp Arg Glu Ala Lys
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 51

Pro Tyr Ala Tyr Trp Met Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (7)..(7)
<223> OTHER INFORMATION: Xaa is Nor-valine (Nva)

<400> SEQUENCE: 52
```

```
Arg Pro Lys Pro Leu Ala Xaa Trp
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: Synthetic target peptide sequence of MMP

<400> SEQUENCE: 53

Pro Leu Ala Tyr Trp Ala Arg
1               5
```

```
<210> SEQ ID NO 54
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 54

Gly Pro Pro Gly Val Val Gly Pro
1               5
```

```
<210> SEQ ID NO 55
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 55

Gly Pro Pro Gly Leu Arg Gly Glu
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 56

Gly Pro Gly Gly Val Val Gly Pro
1               5
```

```
<210> SEQ ID NO 57
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 57

Ile Pro Gln Asn Phe Phe Gly Val
1               5
```

```
<210> SEQ ID NO 58
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 58
```

```
Pro Pro Gly Ala Tyr His Gly Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 59

Arg Pro Lys Pro Gln Gln Phe Trp
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic target peptide sequence of MMP
<220> FEATURE:
<221> NAME/KEY: MISC_FEATURE
<222> LOCATION: (4)..(4)
<223> OTHER INFORMATION: Xaa is Cys(p-OMeBz)

<400> SEQUENCE: 60

Pro Leu Ala Xaa Trp Ala Arg
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic target peptide sequence of MMP

<400> SEQUENCE: 61

Ala Gly Leu Leu Gly Gln Pro Gly
1               5
```

FLUORESCENT CYCLIC PEPTIDES, PREPARATION METHOD THEREOF AND USE OF THESE PEPTIDES FOR MEASURING THE ENZYMATIC ACTIVITY OF A PROTEASE ENZYME

TECHNICAL FIELD

The present invention relates to novel fluorescent cyclic peptides which can be used to measure the enzymatic activity of a protease enzyme, notably with the so-called FRET technique (abbreviation for Fluorescence Resonance Energy Transfer or Förster's Resonance Energy Transfer).

The invention finds particular application in the field of the diagnosis of diseases arising from an enzymatic disorder.

STATE OF THE PRIOR ART

Enzymes have complex mechanisms of action notably involving regulation phenomena which, when disrupted, can be the cause of the onset of pathological disorders.

This is notably the case with metalloproteinases (known under the abbreviation MMP), which are capable of cleaving all the elements of the extracellular matrix, some growth factors and adhesion molecules. These enzymes are naturally regulated by inhibitors such as TIMPs (Tissue inhibitor of metalloproteinases). When the MMP/TIMP equilibrium is disrupted, pathological processes may occur such as tumour growth, metastases, rheumatoid arthritis, heart disease.

Having regard to the involvement of enzymes in numerous pathologies, it was soon proven to be essential to provide tools allowing the activity of these enzymes to be measured, with a view to establishing a possible correlation with the detected pathology. At the current time, the tools available consist of substrates of the enzyme whose activity is to be measured, these substrates having fluorescent groups, the activity thus possibly being quantified by fluorescence measurements. In particular, the fluorescence technique that is most frequently used is the Fluorescence Resonance Energy Transfer technique or FRET. However, this technique is not based as such on measurement of fluorescence transfer but on measurement of the transfer of electronic energy. A distinction must therefore be made between radiative transfer and non-radiative (or resonant) transfer. Radiative transfer does not provide access to information such as the distance between groups, their orientations, which may be essential data for understanding or characterizing the systems being examined.

Radiative transfer is a process which occurs in two steps. At an initial step, a photon is emitted by a donor group, and at a second step this photon is absorbed by a photon-acceptor group the same or different from the donor group. This transfer does not require any interaction between the groups but is dependent on spectral overlapping of the species and of concentration.

Non-radiative transfer of excitation energy requires an interaction between a donor group and an acceptor group. This transfer can only take place if the emission spectrum of the donor group partly overlaps the absorption spectrum of the acceptor group, so that there is energy correspondence between vribonic transitions of the donor group and vibronic transitions of the acceptor group. Said transitions are said to be coupled or « in resonance ».

The phenomenon of non-radiative energy transfer was studied by Förster. He was able to evidence that this physical phenomenon takes place over very short distances, of the order of 10 to 100 Å. When the distance between the donor group and the acceptor group is increased, this translates as a variation in energy transfer. This phenomenon can therefore be used to evaluate the enzymatic activity of a protease enzyme. By placing in contact a substrate comprising both a donor group and an acceptor group, respectively arranged at each of its ends, with a specific protease enzyme this leads to cleavage of the substrate and therefore to an increase in the distance between the donor group and the acceptor group, and hence a variation in the transfer of excitation energy (or resonance energy). On the basis of this variation, it is possible to arrive at estimating the activity of the enzyme.

The substrates currently used are for the most part substrates of linear structure, which have proved to be scarcely stable in a biological medium, since they are notably likely to be degraded by exoproteases and non-specific proteases.

There is a therefore a veritable need for peptides which can be used as tools for quantification of the enzymatic activity of a predetermined protease enzyme, which are stable and which notably allow monitoring of the enzymatic activity of said enzyme using the FRET technique.

DISCLOSURE OF THE INVENTION

The Inventors have therefore developed novel peptides meeting the above-mentioned need.

Therefore, according to a first subject-matter, the invention pertains to a cyclic peptide (also designated as a cyclopeptide) comprising the following sequence:

-$S_1$-$X_1$-$S_2$-$X_2$- wherein $S_1$ is a first target peptide sequence of a protease enzyme $E_1$, $S_2$ is a second target peptide sequence of a protease enzyme $E_2$, $S_1$ and $S_2$ possibly being the same or different, said first peptide sequence $S_1$ and said second peptide sequence $S_2$ comprising 4 to 14 amino acids, $E_1$ and $E_2$ possibly corresponding to the same protease enzyme or to two different protease enzymes, $X_1$ is a probe carrying a fluorescent donor group and $X_2$ is a probe carrying a fluorescent or non-fluorescent acceptor group.

Preferably, the donor group and the acceptor group are chosen so that the fluorescence emission spectrum of the donor group at least partly overlaps the absorption spectrum of the acceptor group.

Therefore, in the presence of one protease enzyme E (if $E_1$ and $E_2$ only form one and the same enzyme and $S_1$ and $S_2$ are target peptide sequences of the same protease enzyme) or of both a protease enzyme $E_1$ and a protease enzyme $E_2$ (if they are different and if $S_1$ is a target peptide sequence of the protease enzyme $E_1$ and $S_2$ is a target peptide sequence of the protease enzyme $E_2$), the cyclic peptides of the invention will be cleaved both at the first peptide sequence $S_1$ and at the second peptide sequence $S_2$, which will generate distancing in space of the probes $X_1$ and $X_2$, on account of the arrangement of the probes $X_1$ and $X_2$. It is followed by distancing of the donor and acceptor groups and hence by a variation in transfer of resonance energy between these two groups. Using the variation in resonance energy, it is therefore possible to arrive at the enzymatic activity of the protease enzyme E or protease enzymes $E_1$ and $E_2$.

Moreover, the fact that the peptides of the invention are cyclic means that it is possible to overcome the drawbacks of linear peptides conventionally used in the prior art, notably the problems of stability encountered with the prior art linear peptides.

According to one particular embodiment of the invention, $E_1$ and $E_2$ correspond to the same protease enzyme.

To study the enzymatic activity of a protease enzyme E, if $E_1=E_2$, the inventors could have quite simply imagined the cyclising of a single linear peptide sequence that is the target of the protease enzyme E to be studied, comprising a probe $X_1$ and a probe $X_2$ at the ends thereof according to the following scheme:

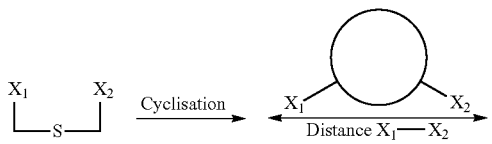

In the presence of the protease enzyme E to be studied, the cyclic peptide would be cleaved as per the following scheme:

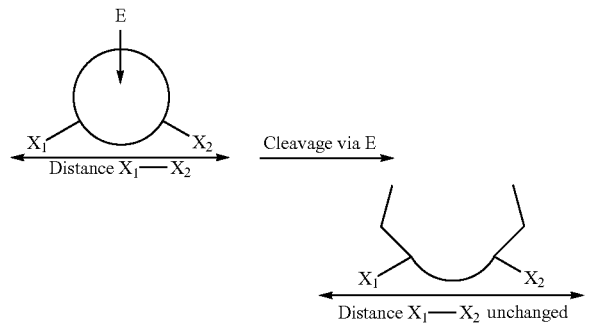

After cleaving, the distance between the groups $X_1$ and $X_2$ remains unchanged. As a result there is no variation in resonance transfer, and hence it is impossible to quantify the activity of the protease enzyme E.

Before entering into the description in more detail, we propose the following definitions.

By fluorescent donor group, is conventionally meant a group capable of absorbing light energy (called excitation light, whose wavelength generally belongs to the ultraviolet region) and of re-emitting emitting this light in two possible forms depending on its environment:

a) in the form of transfer of excitation energy by resonance with an acceptor group, provided that the latter lies at a distance compatible with the FRET phenomenon described previously, and preferably at a distance ranging from 10 to 100 Å; or b) in the form of fluorescent light (called donor emission light) whose wavelength generally belongs to the visible region.

By acceptor group is conventionally meant, in the meaning of the invention, a group capable of absorbing the excitation energy of the donor group by resonance energy. This excitation energy may be re-emitted in two major modes:

a) by radiative emission (emission of photons) in which case the term fluorescent acceptor group will be used; or b) by non-radiative emission (namely any deactivation mode other than the emission of photons), in which case the term non-fluorescent acceptor group will be used.

By probe is conventionally meant, and in the meaning of the invention, an amino acid residue carrying a donor group (for probe $X_1$) or carrying an acceptor group (for probe $X_2$).

By amino acid residue is conventionally meant the residual amino acid resulting from the reaction of a $-NH_2$ function of an amino acid, or $-CO_2H$ and similar, with a function of another compound, so as to form a covalent bond.

By target peptide sequence is conventionally meant, and in the meaning of the invention, a peptide sequence capable of being recognized and cleaved by a protease enzyme.

The use of a cyclic peptide comprising two target peptide sequences of the protease enzyme $E_1$ and of the protease enzyme $E_2$ ($E_1$ and $E_2$ possible being the same or different) between which a probe $X_1$ and a probe $X_2$ conforming to the invention are respectively arranged, makes it possible—as explained above—to provide good tools for quantification of the activity of said protease enzymes.

The cyclic peptides of the invention may meet the following formula:

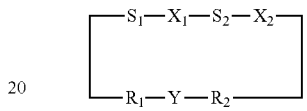

wherein:

$S_1$, $X_1$, $S_2$ and $X_2$ meet the same definition as the one given above;

$R_1$ and $R_2$ independently correspond to a simple bond, an amino acid residue or a peptide sequence;

Y corresponds to a $-CONH-$ or $-NHCO-$ group.

$S_1$ and $S_2$ may be the same, when the peptide is intended to quantify the activity of a single protease enzyme ($E_1$ and $E_2$ the being the same), or they may be different notably when the peptide is intended to differentiate between the presence of isoforms of the same protease enzyme or the presence of two different protease enzymes $E_1$ and $E_2$.

When $S_1$ and $S_2$ are the same, they can be arranged in the same direction or in reverse direction. For example, when $S_1$ corresponds to the sequence -Gly-Pro-Gln-Gly-Leu-Leu-Gly-Ala- (SEQ ID NO: 1), the sequence $S_2$ may correspond to the same sequence arranged in opposite direction, namely the following sequence-Ala-Gly-Leu-Leu-Gly-Gln-Pro-Gly- (SEQ ID NO: 61).

$R_1$ and $R_2$, in one particular embodiment of the invention, may correspond to an amino acid residue or to a peptide sequence. This is particularly advantageous when the cyclic peptides are intended for medication dosage forms, and notably for reasons of stability of the peptides in a biological medium.

The cyclic peptides of the invention are particularly adapted for measuring the enzymatic activity of protease enzymes of MMP type (also known as << extracellular matrix metalloproteases >>).

In this case, the protease enzyme $E_1$ and the protease enzyme $E_2$ are enzymes of MMP type, in which case the first peptide sequence $S_1$ is the target of a MMP protease enzyme and the second peptide sequence $S_2$ is the target of a MMP protease enzyme.

MMPs are a family of endopeptidases, numbering 28, containing a zinc atom at their active site. They can be classified into two sub-families, depending upon whether they are secreted or associated with a membrane. The secreted MMPs comprise collagenases (e.g. MMP-1, 8, 13 and 18), gelatinases (e.g. MMP-2 and 9), matrilysins (e.g. MMP-7 and 26), stromelysins (e.g. MMP-3, 10 and 11), epilysin (MMP-28), enamelysin (MMP-20). The MMPs associated with a membrane comprise transmembrane MMPs such as MMP-14, MMP-15, MMP-16, MMP-17, MMP-23, MMP-24 and MMP-25.

MMPs are capable of cleaving all the elements of the extracellular matrix and some growth factors, or even adhesion molecules. MMPs are regulated by natural inhibitors such as TIMPs and play an important role in physiological processes (such as embryonic growth, angiogenesis, remodelling of bone tissue). When the MMP/TIMP balance is disrupted, pathological processes occur such as tumour growth, metastases, rheumatoid arthritis, heart disease.

The role of MMPs in tumour progression is multiple, notably on account of the capacity of MMPs to degrade the extracellular matrix, thereby promoting tumour invasion. It has been shown that MMPs also have proteolytic activity against non-matrix proteins, conferring a complex role upon them in several other steps of tumour progression, loss of adherence, invasion, proliferation, angiogenesis, intravasion, extravasion and metastatic growth.

Cyclic peptides therefore prove to be excellent tools for monitoring the enzymatic activity of protease enzymes of MMP type, particularly in order to establish links between enzymatic activity and detected pathologies.

More precisely, when the cyclic peptides are intended for the follow-up of MMP activity, the target peptide sequences $S_1$ and $S_2$ will be the target of one MMP enzyme (if $S_1=S_2$ or if $S_1$ and $S_2$ are different target sequences intended to distinguish between two isomorphs of one same enzyme) or of two MMP enzymes (if $S_1$ and $S_2$ are different and respectively targets of two different protease enzymes), these sequences corresponding to sequences of the substrates of the MMP(s) recognized by the MMP(s) whose activity it is desired to monitor.

In particular, the target peptide sequences $S_1$ and $S_2$ can be the targets of a MMP enzyme chosen from among MMP-1, MMP-2, MMP-3, MMP-5, MMP-7, MMP-8, MMP-9, MMP-10, MMP-11, MMP-12, MMP-13, MMP-14, MMP-15, MMP-16, MMP-17, MMP-19, MMP-23, MMP-25 and MMP-26 and mixtures thereof.

The peptide sequences $S_1$ and $S_2$ are linear sequences having a length ranging from 4 to 14 amino acids, which allows the cyclic peptides containing the same to have the necessary conformation to exhibit activity. $S_1$ and $S_2$ are advantageously chosen so that the distance between their N and C terminal ends lies between 10 and 100 Å, said distance being compatible with the effective distance to conduct FRET between a donor group and an acceptor group such as defined previously. The use of molecular modelling software allows reliable prediction of said distance.

The peptide sequences $S_1$ and $S_2$ can be derived from natural peptide sequences found in natural substrates of MMPs, or can derive from synthetic sequences known to be synthetic substrates of MMPs.

Advantageously, the cyclic peptides of the invention only contain natural amino acids, which allows limitation of their possible cytotoxicity and avoids the introduction of non-natural amino acids into the organisms concerned.

In some cases, it is possible that a natural or synthetic substrate is recognized and cleaved by several MMPs. To determine which MMP is responsible for cleavage, it is necessary to use and compare enzymatic kinetic data of the different MMPs for this substrate.

These enzymatic kinetic data which allow discrimination between several MMPs, are generally the Mickaelis constant (Km) which is the indicator of affinity of an enzyme for its substrate, and the ratio of the catalytic constant (Kcat, number of moles of products formed per second and per mole of enzyme) over the Mickaelis constant which is the indicator of the catalytic efficacy of the enzyme. Generally, there therefore exists a specific pair of values (Km and kcat/Km) for a MMP/substrate pair. It is therefore possible for example, when 2 MMPs recognize the same substrate, to determine which one is responsible for the visualized activity.

The synthetic sequences may, for example, comprise the following amino acids or groups:

Nva (Nor-valine); Cha (3-cyclohexylalanine); Dpa (N-3(2, 4-dinitrophenyl)-L-2,3-diaminopropionyl); Abu: α-aminobutyric acid; Cys(Me) corresponding to S-methylcysteine, which means that the —SH group is replaced by the —S—CH$_3$ group, D-Arg corresponding to D-Arginine.

In the remainder of this description, it is specified that the abbreviations listed below have the following meanings:

Gly: glycine; Pro: proline; Leu: leucine; Ala: alanine; Gln: glutamine; Ile: isoleucine; Arg: arginine; Val: valine; Tyr: tyrosine; Glu: glutamate; Met: methionine; Phe: phenylalanine; Asn: Asparagine; Thr: threonine; Trp: tryptophan; Ser: serine; His: histidine, these abbreviations corresponding to the official 3-letter nomenclature for amino acids.

When the first sequence $S_1$ and/or the second sequence $S_2$ are intended to be the target of the MMP-1 enzyme, they may therefore correspond to at least one of the following sequences:

```
                                            SEQ. 1
-Gly-Pro-Gln-Gly-Leu-Leu-Gly-Ala-

SEQ. 2
-Ala-Pro-Gln-Gly-Ile-Ala-Gly-Gln-

SEQ. 3
-Gly-Pro-Gln-Gly-Leu-Ala-Gly-Gln-

SEQ. 4
-Gly-Pro-Leu-Gly-Ile-Ala-Gly-Ile-

SEQ. 5
-Gly-Pro-Glu-Gly-Leu-Arg-Val-Gly-

SEQ. 6
-Tyr-Glu-Ala-Gly-Leu-Gly-Val-Val-

SEQ. 7
-Ala-Gly-Leu-Gly-Val-Val-Glu-Arg-

SEQ. 8
-Ala-Gly-Leu-Gly-Ile-Ser-Ser-Thr-

SEQ. 9
-Gly-Ala-Met-Phe-Leu-Glu-Ala-Ile-

SEQ. 10
-Ile-Pro-Glu-Asn-Phe-Phe-Gly-Val-

SEQ. 11
-Thr-Glu-Gly-Glu-Ala-Arg-Gly-Ser-

SEQ. 12
-Arg-Ala-Ile-His-Ile-Gln-Ala-Glu-

SEQ. 13
-Leu-Arg-Ala-Tyr-Leu-Leu-Pro-Ala-

SEQ. 14
-Gly-Pro-Leu-Gly-Met-Arg-Gly-Leu-
Deng, S. J., et al. 2000. J. Biol. Chem. 275,
31422

SEQ. 15
-Pro-Gln-Gly-Leu-Glu-Ala-Lys-
Beekman, B., et al. 1996. FEBS Lett 390, 221

SEQ. 16
-Pro-Leu-Gly-Leu-Trp-Ala-D-Arg-
Bickett, D. M., et al. 1993. Anal. Biochem. 212,
58 Knight, C. G., et al. 1992. FEBS Lett. 296,
```

263 Darlak, K., et al. 1990. J. Biol. Chem. 265, 5199 Stack, M. S., and Gray, R. D. 1989. J. Biol. Chem. 264, 4277

SEQ. 17
-Pro-Leu-Ala-Leu-Trp-Ala-Arg-
Netzel-Arnett, S., et al. 1991. Anal. Biochem. 195, 86

SEQ. 18
-Pro-Cha-Abu-Cys(Me)-His-Ala-
McGeehan, G. M., et al. 1994. J. Biol. Chem. 269, 32814

SEQ. 19
-Pro-Cha-Gly-Cys(Me)-His-Ala-
Bickett, D. M., et al. 1993. Anal. Biochem. 212, 58

SEQ. 20
-Pro-Cha-Gly-Cys(Me)-His-Ala-
Mohan, M. J. et al. 2002. Biochemistry 41, 9462 Hanessian, S. et al. 2001. J. Med. Chem. 44, 3066 Ambrose, W. P. et al. 1998. Anal. Biochem. 263, 150

SEQ. 21
-Pro-Leu-Gly-Leu-Dpa-Ala-Arg-
Knäuper, V. et al. 1996. J. Biol. Chem. 271, 1544

SEQ. 22
-Pro-Leu-Gly-[2-mercapto-4-methyl-pentanoyl]-Leu-Gly-
Weingarten, H.; Feder, J. 1985. Anal. Biochem. 147, 437 Weingarten, H. et al. 1985. Biochemistry. 24, 6730

SEQ. 17
-Pro-Leu-Ala-Leu-Trp-Ala-Arg-
A. Santala, A. et al. 1999. FEBS Lett. 461, 153-156 Nagase, H. et al. 1994 J. Biol. Chem. 269, 20952-20957

SEQ. 23
-Pro-Leu-Gly-Cys(Me)-His-Ala-D-Arg-
J. Berman et al. 1992. J. Biol. Chem. 267, 1434-1437

SEQ. 24
-Arg-Pro-Leu-Ala-Leu-Trp-Arg-
Kraft, P. J. et al. 2001. Connect. Tissue Res. 42, 149-163 Itoh, M. et al. 1997. J. Pharm. Biomed. Anal. 15, 1417-1426 Welch, A. R. et al. 1995. Arch. Biochem. Biophys. 324, 59-64

SEQ. 25
-Pro-Cha-Gly-Nva-His-Ala-
Lauer-Fields, J. L. and Fields, G. B. 2002 Biol. Chem. 383, 1095-1105 Lauer-Fields, J. L. et al. 2001. Biochemistry 40, 5795-5803

SEQ. 26
-Arg-Pro-Lys-Pro-Tyr-Ala-Nva-Trp-Met-
Bremer, C. et al. 2002. Acad. Radiol. 9 Suppl 2, S314-S315 Nagase, H. et al. 1994. J. Biol. Chem. 269, 20952-20957

When the first sequence $S_1$ and/or the second sequence $S_2$ are intended to be the target of the MMP-2 enzyme, they may therefore correspond to at least one of the following sequences:

SEQ. 10
-Ile-Pro-Glu-Asn-Phe-Phe-Gly-Val-

SEQ. 27
-Pro-Pro-Gly-Ala-Tyr-His-Gly-Ala-

SEQ. 12
-Arg-Ala-Ile-His-Ile-Gln-Ala-Glu-

SEQ. 28
-Gly-Pro-His-Leu-Leu-Val-Glu-Ala-

SEQ. 13
-Leu-Arg-Ala-Tyr-Leu-Leu-Pro-Ala-

SEQ. 29
-Pro-Gln-Gly-Leu-Glu-Ala-Lys-
Beekman, B., et al. 1996. FEBS Lett 390, 221

SEQ. 16
-Pro-Leu-Gly-Leu-Trp-Ala-D-Arg-
Bickett, D. M., et al. 1993. Anal. Biochem. 212, 58 Knight, C. G., et al. 1992. FEBS Lett. 296, 263 Darlak, K., et al. 1990. J. Biol. Chem. 265, 5199 Stack, M. S., and Gray, R. D. 1989. J. Biol. Chem. 264, 4277

SEQ. 30
-Pro-Leu-Ala-Nva-Dpa-Ala-Arg-
Murphy, G., et al. 1994. J. Biol. Chem. 269, 6632

SEQ. 21
-Pro-Leu-Gly-Leu-Dpa-Ala-Arg-
Knight, C. G., et al. 1992. FEBS Lett. 296, 263

SEQ. 31
-Pro-Leu-Gly-Met-Trp-Ser-Arg-
Netzel-Arnett, S., et al. 1991. Anal. Biochem. 195, 86

SEQ. 32
-Pro-Leu-Gly-SCH[$CH_2CH(CH_3)_2$]-CO-Leu-Gly-
Weingarten, H., et al. 1985. Anal. Biochem. 147, 437 Weingarten, H., et al. 1985. Biochemistry 24, 6730

SEQ. 33
-Arg-Pro-Pro-Gly-Phe-Ser-Ala-Phe-
G. D. Johnson and K. Ahn 2000. Anal. Biochem. 286, 112

SEQ. 21
-Pro-Leu-Gly-Leu-Dpa-Ala-Arg-
Knight, C. G. et al. 1992. FEBS Lett. 296, 263

SEQ. 22
-Pro-Leu-Gly-[2-mercapto-4-methyl-pentanoyl]-Leu-Gly-
Weingarten, H.; Feder, J. 1985. Anal. Biochem. 147, 437 Weingarten, H. et al. 1985. Biochemistry. 24, 6730 Xia, T. et al. 1996. Biochim. Biophys. Acta 1293, 259

SEQ. 23
-Pro-Leu-Gly-Cys(Me)-His-Ala-D-Arg-
J. Berman et al., 1992. J. Biol. Chem. 267, 1434-1437

SEQ. 24
-Arg-Pro-Leu-Ala-Leu-Trp-Arg-
Kraft, P. J. et al. 2001. Connect. Tissue Res. 42, 149-163 Itoh, M. et al. 1997. J. Pharm. Biomed. Anal. 15, 1417-1426 Welch, A. R. et al. 1995. Arch. Biochem. Biophys. 324, 59-64

SEQ. 25
-Pro-Cha-Gly-Nva-His-Ala-
Lauer-Fields, J. L. and Fields, G. B. 2002 Biol. Chem. 383, 1095-1105 Lauer-Fields, J. L. et al. 2001. Biochemistry 40, 5795-5803

-continued

-Arg-Pro-Lys-Pro-Tyr-Ala-Nva-Trp-Met- SEQ. 26
Bremer, C. et al. 2002. Acad. Radiol. 9 Suppl
2, S314-S315 Nagase, H. et al. 1994. J. Biol.
Chem. 269, 20952-20957

When the first sequence $S_1$ and/or the second sequence $S_2$ are intended to be the targets of the MMP-3 enzyme, they may therefore correspond to at least one of the following sequences:

-Gly-Pro-Glu-Gly-Leu-Arg-Val-Gly- SEQ. 5

-Arg-Val-Gly-Phe-Tyr-Glu-Ser-Asp- SEQ. 34

-Leu-Leu-Ser-Ala-Leu-Val-Glu-Thr- SEQ. 35

-Glu-Ala-Ile-Pro-Met-Ser-Ile-Pro- SEQ. 36

-Ile-Ala-Gly-Arg-Ser-Leu-Asn-Pro- SEQ. 37

-Ile-Pro-Glu-Asn-Phe-Phe-Gly-Val- SEQ. 10

-Lys-Pro-Gln-Gln-Phe-Phe-Gly-Leu- SEQ. 38

-Asp-Val-Ala-Gln-Phe-Val-Leu-Thr- SEQ. 39

-Asp-Thr-Leu-Glu-Val-Met-Arg-Lys- SEQ. 40

-Asp-Val-Gly-His-Phe-Arg-Thr-Phe- SEQ. 41

-Asp-Ser-Gly-Gly-Phe-Met-Leu-Thr- SEQ. 42

-Arg-Val-Ala-Glu-Met-Arg-Gly-Glu- SEQ. 43

-Asp-Leu-Gly-Arg-Phe-Gln-Thr-Phe- SEQ. 44

-Pro-Phe-Ser-Pro-Leu-Val-Ala-Thr- SEQ. 45

-Leu-Arg-Ala-Tyr-Leu-Leu-Pro-Ala- SEQ. 13

-Ala-Pro-Gly-Asn-Ala-Ser-Glu-Ser- SEQ. 46

-Phe-Ser-Ser-Glu-Ser-Lys-Arg-Glu- SEQ. 47

-Arg-Ala-Ile-His-Ile-Gln-Ala-Glu- SEQ. 12

-Gly-Pro-His-Leu-Leu-Val-Glu-Ala- SEQ. 28

-Pro-Pro-Glu-Glu-Leu-Lys-Phe-Gln- SEQ. 48

-Gly-Pro-Leu-Gly-Met-Arg-Gly-Leu- SEQ. 49
Deng, S. J., et al. 2000. J. Biol. Chem. 275, 31422

-Pro-Gln-Gly-Leu-Glu-Ala-Lys- SEQ. 15
Beekman, B., et al. 1996. FEBS Lett 390, 221

-Arg-Pro-Lys-Pro-Val-Glu-Nva-Trp-Arg-Glu-Ala-Lys- SEQ. 50
Beekman, B., et al. 1997. FEBS Lett 418, 305

-Pro-Leu-Gly-Leu-Trp-Ala-D-Arg- SEQ. 16
Bickett, D. M., et al. 1993. Anal. Biochem. 212, 58 Knight, C. G., et al. 1992. FEBS Lett. 296, 263 Darlak, K., et al. 1990. J. Biol. Chem. 265, 5199 Stack, M. S., and Gray, R. D. 1989. J. Biol. Chem. 264, 4277

-Pro-Tyr-Ala-Tyr-Trp-Met-Arg- SEQ. 51
Netzel-Arnett, S., et al. 1991. Anal. Biochem. 195, 86

-Arg-Pro-Lys-Pro-Leu-Ala-Nva-Trp- SEQ. 52
Bickett, D. M., et al. 1994. Ann. N. Y. Acad. Sci. 732, 351

-Pro-Cha-Gly-Cys(Me)-His-Ala- SEQ. 20
Mohan, M. J. et al. 2002. Biochemistry 41, 9462 Hanessian, S. et al. 2001. J. Med. Chem. 44, 3066 Ambrose, W. P. et al. 1998. Anal. Biochem. 263, 150

-Pro-Leu-Gly-Leu-Dpa-Ala-Arg- SEQ. 21
Knight, C. G. et al. 1992. FEBS Lett. 296, 263

-Pro-Leu-Gly-[2-mercapto-4-methyl-pentanoyl]-Leu-Gly- SEQ. 22
Weingarten, H.; Feder, J. 1985. Anal. Biochem. 147, 437 Weingarten, H. et al. 1985. Biochemistry. 24, 6730

-Arg-Pro-Lys-Pro-Tyr-Ala-Nva-Trp-Met- SEQ. 26
Bremer, C. et al. 2002. Acad. Radiol. 9 Suppl 2, S314-S315 Nagase, H. et al. 1994. J. Biol. Chem. 269, 20952-20957

-Arg-Pro-Lys-Pro-Val-Glu-Nva-Trp-Arg- SEQ. 50
Bremer, C. et al. 2002. Acad. Radiol. 9 Suppl 2, S314-S315 Nagase, H. et al. 1994. J. Biol. Chem. 269, 20952-20957

When the first sequence $S_1$ and/or the second sequence $S_2$ are intended to be the target of the MMP-5 enzyme, they may therefore correspond to at least one of the following sequences:

-Arg-Pro-Lys-Pro-Val-Glu-Nva-Trp-Arg-Glu-Ala-Lys- SEQ. 50
Beekman, B., et al. 1997. FEBS Lett 418, 305

When the first sequence $S_1$ and/or the second sequence $S_2$ are intended to be the target of the MMP-7 enzyme, they may therefore correspond to at least one of the following sequences:

SEQ. 16
-Pro-Leu-Gly-Leu-Trp-Ala-D-Arg-
Bickett, D. M., et al. 1993. Anal. Biochem. 212,
58 Knight, C. G., et al. 1992. FEBS Lett. 296,
263 Darlak, K., et al. 1990. J. Biol. Chem. 265,
5199 Stack, M. S., and Gray, R. D. 1989. J.
Biol. Chem. 264, 4277

SEQ. 21
-Pro-Leu-Gly-Leu-Dpa-Ala-Arg-
Knight, C. G., et al. 1992. FEBS Lett. 296, 263

SEQ. 24
-Arg-Pro-Leu-Ala-Leu-Trp-Arg-Ser-
Welch, A. R., et al. 1996. Biochemistry 35,
10103 Welch, A. R., et al. 1995. Arch. Biochem.
Biophys. 324, 59

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44,
3066 Ambrose, W. P. et al. 1998. Anal. Biochem.
263, 150

SEQ. 22
-Pro-Leu-Gly-[2-mercapto-4-methyl-pentanoyl]-
Leu-Gly-
Weingarten, H.; Feder, J. 1985. Anal. Biochem.
147, 437 Weingarten, H. et al. 1985. Biochem-
istry. 24, 6730

SEQ. 17
-Pro-Leu-Ala-Leu-Trp-Ala-Arg-
A. Santala, A. et al. 1999. FEBS Lett. 461,
153-156 Shabani, F. et al. 1998. Free Radic.
Res. 28, 115-123 Nagase, H. et al. 1994 J.
Biol. Chem. 269, 20952-20957

SEQ. 51
-Pro-Tyr-Ala-Tyr-Trp-Met-Arg-
Finch-Arietta, M. et al., 1993. Agents Actions
39 SpecNo, C189-C191 Netzel-Arnett, S. et al.
1991 Anal. Biochem. 195, 86-92

SEQ. 52
-Arg-Pro-Lys-Pro-Leu-Ala-Nva-Trp-
Finch-Arietta, M. et al., 1993. Agents Actions
39 SpecNo, C189-C191 Bickett, D. M. et al.,
1994. Ann. N. Y. Acad. Sci. 732, 351-355

When the first sequence $S_1$ and/or the second sequence $S_2$ are intended to be the target of the MMP-8 enzyme, they may therefore correspond to at least one of the following sequences:

SEQ. 53
-Pro-Leu-Ala-Tyr-Trp-Ala-Arg-
Netzel-Arnett, S., et al. 1991. Anal. Biochem.
195, 86

SEQ. 16
-Pro-Leu-Gly-Leu-Trp-Ala-D-Arg-
Grams, F. et al. 2001. Biol. Chem. 382, 1277

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44,
3066 Ambrose, W. P. et al. 1998. Anal. Biochem.
263, 150

SEQ. 21
-Pro-Leu-Gly-Leu-Dpa-Ala-Arg-
Knäuper, V. et al. 1996. J. Biol. Chem. 271,
1544

SEQ. 22
-Pro-Leu-Gly-[2-mercapto-4-methyl-pentanoyl]-
Leu-Gly-
Weingarten, H.; Feder, J. 1985. Anal. Biochem.
147, 437 Weingarten, H. et al. 1985. Biochem-
istry. 24, 6730

SEQ. 17
-Pro-Leu-Ala-Leu-Trp-Ala-Arg-
A. Santala, A. et al. 1999. FEBS Lett. 461,
153-156 Shabani, F. et al. 1998. Free Radic.
Res. 28, 115-123 Nagase, H. et al. 1994 J.
Biol. Chem. 269, 20952-20957

SEQ. 23
-Pro-Leu-Gly-Cys(Me)-His-Ala-D-Arg-
J. Berman et al., 1992. J. Biol. Chem. 267,
1434-1437

SEQ. 24
-Arg-Pro-Leu-Ala-Leu-Trp-Arg-
Kraft, P. J. et al. 2001. Connect. Tissue Res.
42, 149-163 Itoh, M. et al. 1997. J. Pharm.
Biomed. Anal. 15, 1417-1426 Welch, A. R. et al.
1995. Arch. Biochem. Biophys. 324, 59-64

SEQ. 25
-Pro-Cha-Gly-Nva-His-Ala-
Lauer-Fields, J. L. and Fields, G. B. 2002
Biol. Chem. 383, 1095-1105 Lauer-Fields, J. L.
et al. 2001. Biochemistry 40, 5795-5803

When the first sequence $S_1$ and/or the second sequence $S_2$ are intended to be the target of the MMP-9 enzyme, they may therefore correspond to at least one of the following sequences:

SEQ. 54
-Gly-Pro-Pro-Gly-Val-Val-Gly-Pro-

SEQ. 55
-Gly-Pro-Pro-Gly-Leu-Arg-Gly-Glu-

SEQ. 56
-Gly-Pro-Gly-Gly-Val-Val-Gly-Pro-

SEQ. 57
-Ile-Pro-Gln-Asn-Phe-Phe-Gly-Val-

SEQ. 58
-Pro-Pro-Gly-Ala-Tyr-His-Gly-Ala-

SEQ. 12
-Arg-Ala-Ile-His-Ile-Gln-Ala-Glu-

SEQ. 14
-Gly-Pro-Leu-Gly-Met-Arg-Gly-Leu-
Deng, S. J., et al. 2000. J. Biol. Chem. 275,
31422

SEQ. 15
-Pro-Gln-Gly-Leu-Glu-Ala-Lys-
Beekman, B., et al. 1996. FEBS Lett 390, 221

SEQ. 50
-Arg-Pro-Lys-Pro-Val-Glu-Nva-Trp-Arg-Glu-Ala-
Lys-
Beekman, B., et al. 1997. FEBS Lett 418, 305

SEQ. 16
-Pro-Leu-Gly-Leu-Trp-Ala-D-Arg-
Bickett, D. M., et al. 1993. Anal. Biochem.
212, 58 Knight, C. G., et al. 1992. FEBS Lett.
296, 263 Darlak, K., et al. 1990. J. Biol.
Chem. 265, 5199 Stack, M. S., and Gray, R. D.
1989. J. Biol. Chem. 264, 4277

-continued

SEQ. 19
-Pro-Cha-Gly-Cys(Me)-His-Ala-
Bickett, D. M., et al. 1993. Anal. Biochem.
212, 58

SEQ. 32
-Pro-Leu-Gly-SCH[CH$_2$CH(CH$_3$)$_2$]-CO-Leu-Gly-
Weingarten, H., et al. 1985. Anal. Biochem.
147, 437 Weingarten, H., et al. 1985. Biochemistry 24, 6730

SEQ. 33
-Arg-Pro-Pro-Gly-Phe-Ser-Ala-Phe-
G. D. Johnson and K. Ahn 2000. Anal. Biochem.
286, 112

SEQ. 20
-Pro-Cha-Gly-Cys(Me)-His-Ala-
Mohan, M. J. et al. 2002. Biochemistry 41,
9462 Hanessian, S. et al. 2001. J. Med.
Chem. 44, 3066 Ambrose, W. P. et al. 1998.
Anal. Biochem. 263, 150

SEQ. 21
-Pro-Leu-Gly-Leu-Dpa-Ala-Arg-
Roy, N. et al. 1999. Prot. Expr. Purif. 16,
324

SEQ. 22
-Pro-Leu-Gly-[2-mercapto-4-methyl-pentanoyl]-
Leu-Gly-
Weingarten, H.; Feder, J. 1985. Anal. Biochem.
147, 437 Weingarten, H. et al. 1985. Biochemistry. 24, 6730 Xia, T. et al. 1996. Biochim.
Biophys. Acta 1293, 259

SEQ. 23
-Pro-Leu-Gly-Cys(Me)-His-Ala-D-Arg-
J. Berman et al., 1992. J. Biol. Chem. 267,
1434-1437

When the first sequence S$_1$ and/or the second sequence S$_2$ are intended to be the target of the MMP-10 enzyme, they may therefore correspond to at least one of the following sequences:

SEQ. 12
-Arg-Ala-Ile-His-Ile-Gln-Ala-Glu-

SEQ. 28
-Gly-Pro-His-Leu-Leu-Val-Glu-Ala-

SEQ. 21
-Pro-Leu-Gly-Leu-Dpa-Ala-Arg-
Kannan, R. et al. 1999. Prot. Expr. Purif. 16, 76

When the first sequence S$_1$ and/or the second sequence S$_2$ are intended to be the target of the MMP-11 enzyme, they may therefore correspond to at least one of the following sequences:

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44, 3066
Ambrose, W. P. et al. 1998. Anal. Biochem. 263,
150

SEQ. 21
-Pro-Leu-Gly-Leu-Dpa-Ala-Arg-
Kannan, R. et al. 1999. Prot. Expr. Purif. 16, 76

When the first sequence S$_1$ and/or the second sequence S$_2$ are intended to be the target of the MMP-12 enzyme, they may therefore correspond to at least one of the following sequences:

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44, 3066
Ambrose, W. P. et al. 1998. Anal. Biochem. 263, 150

SEQ. 21
-Pro-Leu-Gly-Leu-Dpa-Ala-Arg-
Park, H. I. et al. 2000. J. Biol. Chem. 275, 20540

SEQ. 22
-Pro-Leu-Gly-[2-mercapto-4-methyl-pentanoyl]-Leu-
Gly-
Weingarten, H.; Feder, J. 1985. Anal. Biochem.
147, 437
Weingarten, H. et al. 1985. Biochemistry. 24, 6730

SEQ. 17
-Pro-Leu-Ala-Leu-Trp-Ala-Arg-
A. Santala, A. et al. 1999. FEBS Lett. 461, 153-156
Shabani, F. et al. 1998. Free Radic. Res. 28, 115-123
Nagase, H. et al. 1994 J. Biol. Chem. 269,
20952-20957

SEQ. 23
-Pro-Leu-Gly-Cys(Me)-His-Ala-D-Arg-
Berman, J. et al., 1992. J. Biol. Chem. 267,
1434-1437

SEQ. 51
-Pro-Tyr-Ala-Tyr-Trp-Met-Arg-
Finch-Arietta, M. et al., 1993. Agents Actions 39
SpecNo, C189-C191
Netzel-Arnett, S. et al. 1991 Anal. Biochem. 195,
86-92

SEQ. 52
-Arg-Pro-Lys-Pro-Leu-Ala-Nva-Trp-
Finch-Arietta, M. et al., 1993. Agents Actions 39
SpecNo, C189-C191
Bickett, D. M. et al., 1994. Ann. N.Y. Acad. Sci.
732, 351-355

SEQ. 24
-Arg-Pro-Leu-Ala-Leu-Trp-Arg-
Kraft, P. J. et al. 2001. Connect. Tissue Res. 42,
149-163
Itoh, M. et al. 1997. J. Pharm. Biomed. Anal. 15,
1417-1426
Welch, A. R. et al. 1995. Arch. Biochem. Biophys.
324, 59-64

SEQ. 25
-Pro-Cha-Gly-Nva-His-Ala-
Lauer-Fields, J. L. and Fields,
G. B. 2002 Biol.Chem.
383, 1095-1105
Lauer-Fields, J. L. et al. 2001. Biochemistry 40,
5795-5803

SEQ. 26
-Arg-Pro-Lys-Pro-Tyr-Ala-Nva-Trp-Met-
Bremer, C. et al. 2002. Acad. Radiol. 9 Suppl 2,
S314-S315
Nagase, H. et al. 1994. J. Biol. Chem. 269,
20952-20957

SEQ. 50
-Arg-Pro-Lys-Pro-Val-Glu-Nva-Trp-Arg-
Bremer, C. et al. 2002. Acad. Radiol. 9 Suppl 2,
S314-S315
Nagase, H. et al. 1994. J. Biol. Chem. 269,
20952-20957

SEQ. 59
-Arg-Pro-Lys-Pro-Gln-Gln-Phe-Trp-
Bickett, D. M. et al. 1994. Ann. N.Y. Acad. Sci.
732, 351-355

When the first sequence $S_1$ and/or the second sequence $S_2$ are intended to be the target of the MMP-13 enzyme, they may therefore correspond to at least one of the following sequences:

SEQ. 49
-Gly-Pro-Leu-Gly-Met-Arg-Gly-Leu-
Deng, S. J., et al. 2000. J. Biol. Chem. 275, 31422

SEQ. 50
-Arg-Pro-Lys-Pro-Val-Glu-Nva-Trp-Arg-Glu-Ala-Lys-
Beekman, B., et al. 1997. FEBS Lett 418, 305

SEQ. 25
-Pro-Cha-Gly-Nva-His-Ala-Dpa-
Knauper, V., et al. 1996. J. Biol. Chem. 271, 1544

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44, 3066
Ambrose, W.P. et al. 1998. Anal. Biochem. 263, 150

SEQ. 21
-Pro-Leu-Gly-Leu-Dpa-Ala-Arg-
Knauper, V. et al. 1996. J. Biol. Chem. 271, 1544

SEQ. 22
-Pro-Leu-Gly-[2-mercapto-4-methyl-pentanoyl]-Leu-Gly-
Weingarten, H.; Feder, J. 1985. Anal. Biochem. 147, 437
Weingarten, H. et al. 1985. Biochemistry. 24, 6730

SEQ. 16
-Pro-Leu-Gly-Leu-Trp-Ala-D-Arg-
Netzel-Arnett, S. et al. 1991. Anal. Biochem. 195, 86-92
Santala, A. et al. 1999. FEBS Lett. 461, 153-156
Bickett, D. M. et al., 1993. Anal. Biochem. 212, 58-64

SEQ. 17
-Pro-Leu-Ala-Leu-Trp-Ala-Arg-
A. Santala, A. et al. 1999. FEBS Lett. 461, 153-156
Shabani, F. et al. 1998. Free Radic. Res. 28, 115-123
Nagase, H. et al. 1994 J. Biol. Chem. 269, 20952-20957

SEQ. 23
-Pro-Leu-Gly-Cys(Me)-His-Ala-D-Arg-
J. Berman et al., 1992. J. Biol. Chem. 267, 1434-1437

SEQ. 31
-Pro-Leu-Gly-Met-Trp-Ser-Arg-
Netzel-Arnett, S. et al. 1991. Anal. Biochem. 195, 86-92
d'Ortho, M. P. et al. 1997. Eur. J. Biochem. 250, 751-757

SEQ. 51
-Pro-Tyr-Ala-Tyr-Trp-Met-Arg-
Finch-Arietta, M. et al., 1993. Agents Actions 39 SpecNo, C189-C191
Netzel-Arnett, S. et al. 1991 Anal. Biochem. 195, 86-92

SEQ. 52
-Arg-Pro-Lys-Pro-Leu-Ala-Nva-Trp-
Finch-Arietta, M. et al., 1993. Agents Actions 39 SpecNo, C189-C191
Bickett, D. M. et al., 1994. Ann. N.Y. Acad. Sci. 732, 351-355

SEQ. 24
-Arg-Pro-Leu-Ala-Leu-Trp-Arg-
Kraft, P. J. et al. 2001. Connect. Tissue Res. 42, 149-163
Itoh, M. et al. 1997. J. Pharm. Biomed. Anal. 15, 1417-1426
Welch, A. R. et al. 1995. Arch.Biochem. Biophys. 324, 59-64

SEQ. 53
-Pro-Leu-Ala-Tyr-Trp-Ala-Arg-
Aschi, M. et al. 2002. J. Comput. Aided Mol. Des 16, 213-225
Netzel-Arnett, S. et al. 1991. Anal. Biochem. 195, 86-92

SEQ. 25
-Pro-Cha-Gly-Nva-His-Ala-
Lauer-Fields, J. L. and Fields, G. B. 2002 Biol. Chem. 383, 1095-1105
Lauer-Fields, J. L. et al. 2001. Biochemistry 40, 5795-5803

SEQ. 26
-Arg-Pro-Lys-Pro-Tyr-Ala-Nva-Trp-Met-
Bremer, C. et al. 2002. Acad. Radiol. 9 Suppl 2, S314-S315
Nagase, H. et al. 1994. J. Biol. Chem. 269, 20952-20957

SEQ. 59
-Arg-Pro-Lys-Pro-Gln-Gln-Phe-Trp-
Bickett, D. M. et al. 1994. Ann. N.Y. Acad. Sci. 732, 351-355

When the first sequence $S_1$ and/or the second sequence $S_2$ are intended to be the target of the MMP-14 enzyme, they may therefore correspond to at least one of the following sequences:

SEQ. 60
-Pro-Leu-Ala-Cys(p-OMeBz)-Trp-Ala-Arg-
Mucha, A., et al. 1998. J. Biol. Chem. 273, 2763
Holtz, B., et al. 1999. Biochemistry 38, 12174

SEQ. 20
-Pro-Cha-Gly-Cys(Me)-His-Ala-
Mohan, M. J. et al. 2002. Biochemistry 41, 9462
Hanessian, S. et al. 2001. J. Med. Chem. 44, 3066
Ambrose, W. P. et al. 1998. Anal. Biochem. 263, 150

SEQ. 21
-Pro-Leu-Gly-Leu-Dpa-Ala-Arg-
Roderfeld, M. et al. 2000 . Prot. Expr. Purif. 19, 369
Kannan, R. et al. 1999. Prot. Expr. Purif. 16, 76

SEQ. 22
-Pro-Leu-Gly-[2-mercapto-4-methyl-pentanoyl]-Leu-Gly-
Weingarten, H.; Feder, J. 1985. Anal. Biochem. 147, 437
Weingarten, H. et al. 1985. Biochemistry. 24, 6730

When the first sequence $S_1$ and/or the second sequence $S_2$ are intended to be the target of the MMP-15 enzyme, they may therefore correspond to at least one of the following sequences:

SEQ. 21
-Pro-Leu-Gly-Leu-Dpa-Ala-Arg-
Xue, C.-B. et al. 2001. J. Med. Chem. 44, 2636

When the first sequence $S_1$ and/or the second sequence are intended to be the target of the MMP-16 enzyme, they may therefore correspond to at least one of the following sequences:

```
                                                 SEQ. 21
-Pro-Leu-Gly-Leu-Dpa-Ala-Arg-
Shimada, T. et al. 1999. Eur. J. Biochem. 262, 907
Xue, C.-B. et al. 2001. J. Med. Chem. 44, 2636
```

When the first sequence $S_1$ and/or the second sequence $S_2$ are intended to be the target of the MMP-17 enzyme, they may therefore correspond to at least one of the following sequences:

```
                                                 SEQ. 21
-Pro-Leu-Gly-Leu-Dpa-Ala-Arg-
English, W. R. et al. 2001. FEBS Lett. 491, 137
```

```
                                                 SEQ. 22
-Pro-Leu-Gly-[2-mercapto-4-methyl-pentanoyl]-Leu-
Gly-
```

When the first sequence $S_1$ and/or the second sequence $S_2$ are intended to be the target of the MMP-19 enzyme, they may therefore correspond to at least one of the following sequences:

```
                                                 SEQ. 21
-Pro-Leu-Gly-Leu-Dpa-Ala-Arg-
Pendás, A. M. et al. 1997. J. Biol. Chem. 272, 4281
```

When the first sequence $S_1$ and/or the second sequence $S_2$ are intended to be the target of the MMP-23 enzyme, they may therefore correspond to at least one of the following sequences:

```
                                                 SEQ. 21
-Pro-Leu-Gly-Leu-Dpa-Ala-Arg-
Velasco, G. et al. 1999. J. Biol. Chem. 274, 4570
```

When the first sequence $S_1$ and/or the second sequence $S_2$ are intended to be the target of the MMP-25 enzyme, they may therefore correspond to at least one of the following sequences:

```
                                                 SEQ. 21
-Pro-Leu-Gly-Leu-Dpa-Ala-Arg-
English, W. R. et al. 2001. FEBS Lett. 491, 137
```

When the first sequence $S_1$ and/or the second sequence $S_2$ are intended to be the target of the MMP-26 enzyme, they may therefore correspond to at least one of the following sequences:

```
                                                 SEQ. 16
-Pro-Leu-Gly-Leu-Trp-Ala-D-Arg-
Park, H. I. et al. 2002. J. Biol. Chem. 277, 35168
```

As arises from the foregoing, a given MMP is able to recognize several sequences, these sequences originally belonging to different proteins which, following precise mechanisms, are involved in some pathologies.

As mentioned above, the cyclic peptides of the invention comprise at least one probe $X_1$ carrying a fluorescent donor group and at least one probe $X_2$ carrying a fluorescent or non-fluorescent acceptor group. These are generally chosen so that the fluorescence emission spectrum of the donor group overlaps, at least in part, the absorption spectrum of the acceptor group, which translates as a phenomenon of non-radiative transfer of excitation energy from the donor group to the acceptor group (or resonance energy transfer).

Said groups conventionally comprise an aromatic nucleus e.g. a benzene, anthracene or coumarin nucleus.

As examples, the following pairs may be cited (the first member of the pair being the donor group, whilst the second member of the pair is the acceptor group):
* Tryptophan/2,4-dinitrophenyl (symbolised by the abbreviation W/Dnp);
* o-aminobenzoic acid/2,4-dinitrophenyl (symbolised by the abbreviation Abz/Dnp);
* (7-methoxycoumarin-4-yl)-acetyl/2,4-dinitrophenyl (symbolised by the abbreviation Mca/Dnp);
* (7-methoxycoumarin-4-yl)-acetyl/N-3-(2,4-dinitrophenyl)-L-2,3-diaminopropyl (symbolised by the abbreviation Mca/Dpa);
* Tryptophan/Dansyl (symbolised by the abbreviation W/Dns);
* N-methylanthranoyl/2,4-dinitrophenyl (symbolised by the abbreviation Nma/Dnp);
* 6,7-dimethoxycoumarin-4-yl-acetyl/6-N-(7-nitrobenz-2-oxa-1,3-diazol-4-yl)aminohexanoic acid (symbolized by the abbreviation DMC/Nbd);
* 5-(2'-aminomethyl)naphtalene sulphonic acid/4-(4'-dimethylaminophenylaza)benzoic acid (symbolized by the abbreviation EDANS/Dabcyl);
* 7-methoxycoumarin-3-carboxylic acid/7-diethylaminocoumarin-3-carboxylic acid (symbolised by the abbreviation MC/DAC), said groups meeting the following formulas:

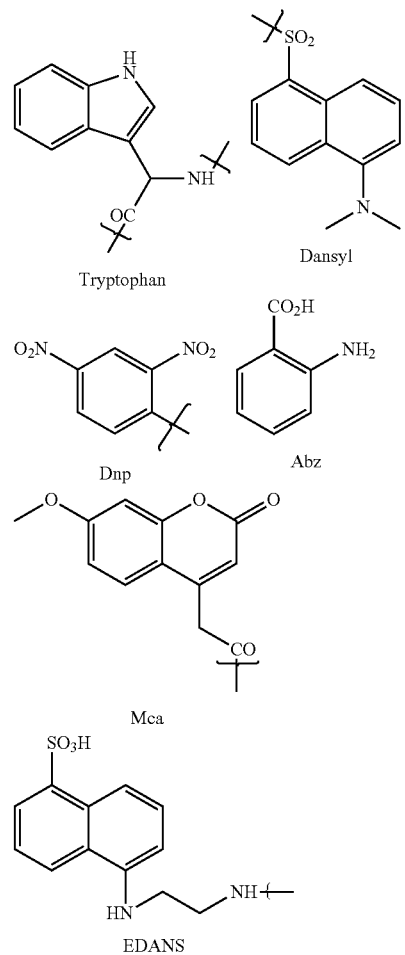

-continued

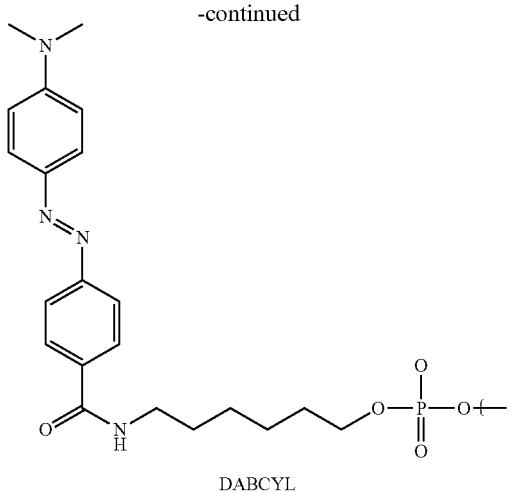

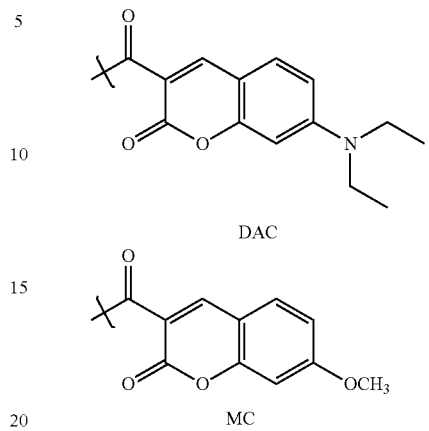

In particular, the preferred pair may be the MC/DAC pair which, once bound to the probe, have the following formulas:

The X₁ and X₂ probes may be amino acid residues.

One example of an X₁ probe can therefore be the -Lys(MC)- probe having the following formula:

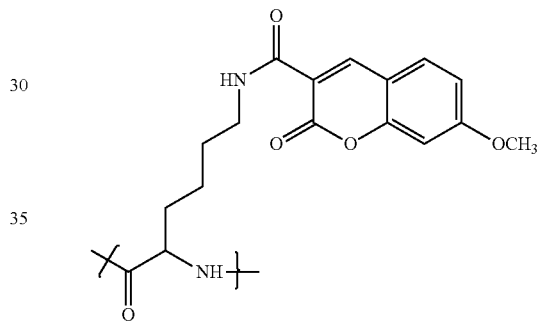

whilst an example of the X₂ probe may be the -Lys(DAC)- probe having the following formula:

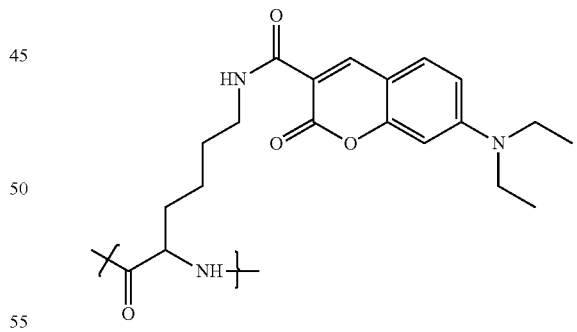

S₁ and S₂ may correspond to a target sequence of an MMP such as defined above, in particular to the following sequence:

```
                                              (SEQ ID NO: 1)
-Gly-Pro-Gln-Gly-Leu-Leu-Gly-Ala-
or
                                             (SEQ ID NO: 57)
-Gly-Pro-Gly-Gly-Val-Val-Gly-Pro
``` these sequences respectively corresponding to sequences recognized by the MMP-1 enzyme and MMP-9 enzyme.

Advantageously, the donor group and the acceptor group are groups comprising a coumarin nucleus.

Since these groups have a common aromatic unit of coumarin type, this allows the formation of a complex of hydrophobic type or π-stacking type, which takes part in the stability of the cyclic peptides of the invention.

A cyclic peptide of the invention may be a cyclic peptide having the following formula:

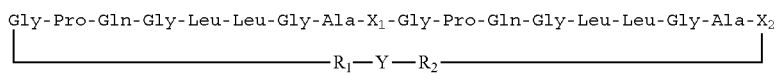

$X_1$, $X_2$, $R_1$, Y and $R_2$ meeting the same definition as the one given above.

A precise cyclic peptide conforming to the invention meets the following formula:

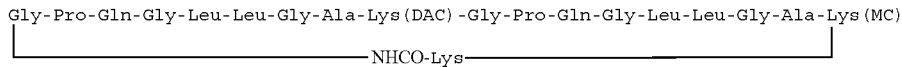

the groups -Lys(DAC)- and -Lys(MC)- meeting the same definition as the one given above.

The sequences in bold will be cleaved in the presence of the MMP1 enzyme, thereby contributing towards distancing the probes Lys(Dac) and Lys(MC) away from one another. This is followed by a variation in resonance transfer, thereby allowing quantification of the activity of the MMP1 enzyme.

The cyclic peptides of the invention, via pendant functions (such as amine functions derived from a lysine or aspartic acid residue) may be led to being fixed onto a carrier, such as particles.

The cyclic peptides of the invention may be prepared with methods involving an automatic synthesis step on a solid phase using a conventional process, followed by coupling of the ends of the linear peptide, either after having released the peptide from the solid phase, or by releasing it afterwards from the solid phase.

The solid phase is conventionally a resin carrying groups capable of reacting with a —$NH_2$ or —COOH function so as to form a covalent bond, this bond being intended to be subsequently cleaved so as to release the peptide once synthesized.

Said resins may be trityl, 2-chloro chloro trityl resins respectively carrying groups of the following formulas:

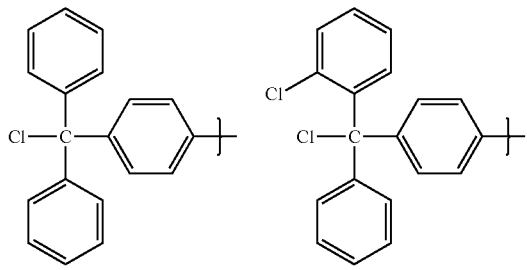 [SMILES: Cc1ccc(C(Cl)(c2ccccc2)c2ccccc2)cc1 ; Cc1ccc(C(Cl)(c2ccccc2)c2ccccc2Cl)cc1]

the curved brackets indicating the point via which the above-mentioned groups are attached to the resin.

According to a first embodiment, the method of the invention comprises:
a) a preparation step, to prepare a linear peptide by chemical synthesis on a solid phase;
b) a release step, to release the linear peptide from the solid phase; and
c) a coupling step, to couple the ends of the linear peptide to form the cyclic peptide.

According to a second embodiment, the method of the invention comprises:

a) a preparation step, to prepare the linear peptide by chemical synthesis on a solid phase;
b) a coupling step, to couple the free end of the linear peptide with a terminal function of a linear residue of the linear peptide; and
c) a release step, to release the cyclic peptide from the solid phase, the steps b) and c) possibly being conducted concomitantly.

Whether for the first embodiment or the second embodiment, when performing step a), the first phase consists of anchoring a first amino acid on the solid phase.

This anchoring can be performed in several manners:
anchoring on the solid phase via a C-terminal end of the first amino acid;
anchoring on the solid phase via the side chain of the first amino acid;
anchoring on the solid phase via the main chain of the first amino acid.

For the first type of anchoring, once the peptide is synthesized, the deprotected N-terminal function of the peptide reacts, as per a nucleophilic addition mechanism, on the carboxyl function that is released or still anchored on the resin. If the carboxyl function is still anchored on the resin, the nucleophilic addition reaction (being an intramolecular addition) jointly produces cyclisation and release of the peptide from the resin.

The second type of anchoring occurring via the side chain of an amino acid, generally devolves upon the following amino acids: asparagine, aspartic acid, glutamine, glutamate, lysine, histidine, serine, threonine, arginine and tyrosine, which have the particularity of having a side chain carrying a function such as —$CO_2H$, OH, $NH_2$ ou $NH_2CO$, capable of reacting with a reactive group carried by the resin.

For the third approach based on anchoring of the main chain on the resin, the synthesized peptide is bound to the resin by one of the nitrogen atoms of an amide link of the main chain.

Evidently those skilled in the art, to synthesize the desired sequence, will use appropriate protector groups.

As mentioned above, the cyclic peptides of the invention are intended to be used to monitor the activity of a protease enzyme E.

More precisely, the use of the cyclic peptides of the invention can be envisaged in several manners:
they may allow correlations to be defined between the activity of an enzyme and a detected pathology;
they can be used to diagnose a pathology, by performing an assay of an enzyme present in a biological sample, if the correlation between the activity of the enzyme and the pathology to be detected is known.

They can notably be used to perform in vitro analysis of fluids comprising the enzyme whose activity it is desired to estimate.

They may also be given in vivo use, notably when the $X_1/X_2$ pair emits in the red.

The invention therefore relates to a ready-to-use reagent comprising at least one cyclic peptide conforming to the invention, and a kit comprising:
- a first compartment comprising at least one cyclic peptide conforming to the invention; and
- a second compartment comprising a buffer solution.

This kit is intended for the preparation of stock solutions, which are to be placed in contact with the protease enzyme whose activity is to be measured. The protease enzyme may be contained in a biological fluid.

As its name suggests, the buffer solution is intended to fix the pH of a solution, so that this pH is neither too acid nor too basic, which would have an influence on subsequent measurements of enzymatic activity.

Finally, the invention relates to the use of at least one cyclic peptide according to the invention, for in vitro determination of the activity of at least one protease enzyme.

Other characteristics and advantages of the invention will become apparent on reading the following examples given by way of illustration and which are non-limiting.

BRIEF DESCRIPTION OF THE DRAWINGS

FIG. 1 is a graph showing the variation in intensity of fluorescence $\Delta_{IF\ donor}$ (in a.u) of a cyclic peptide of

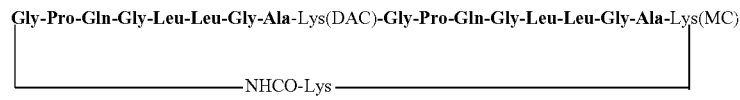

prepared according to the example, as a function of time t (in min), this cyclic peptide being placed, at a concentration of 90 μM, in the presence of a MMP-1 solution (1 nM).

Figure 2:
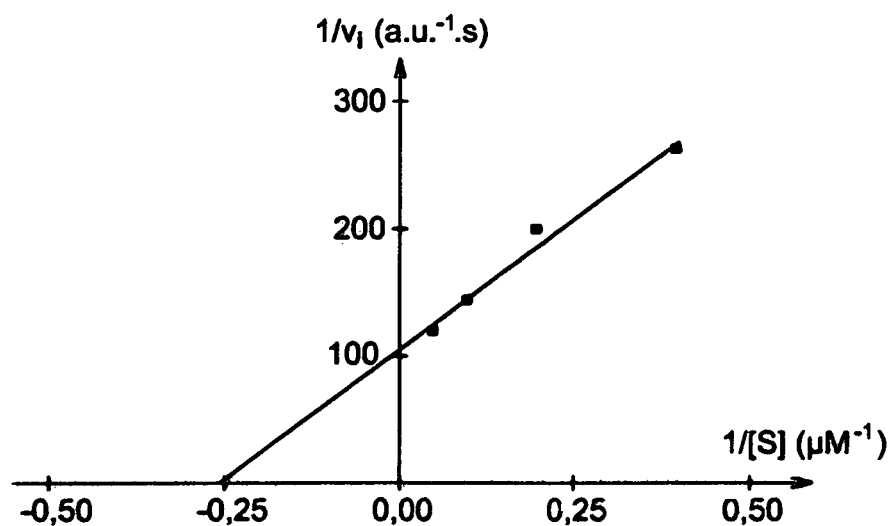

FIG. 2 is a double reciprocal plot showing the inverse of initial hydrolysis velocities $(1/v_i)$ (in $a.u.^{-1} \cdot s$) of a prepared cyclic peptide of

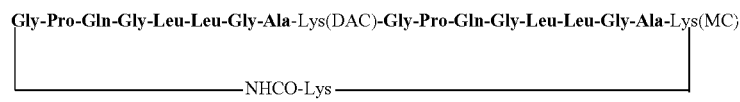

as a function of the inverse of its concentration (1/[S]) (in $\mu M^{-1}$).

DETAILED DESCRIPTION OF PARTICULAR EMBODIMENTS

The following example illustrates the preparation of a cyclic peptide according to the invention comprising two peptide sequences $S_1$ and $S_2$ each corresponding to a MMP1 target sequence, this sequence being the following: -Gly-Pro-Gln-Gly-Leu-Leu-Gly-Ala- (SEQ ID NO: 1).

The preparation of this cyclic peptide comprises the following steps:
a) synthesis of a starting amino acid intended to be grafted onto a resin via its side chain: Fmoc-Lys-OAllyl;
b) grafting said starting amino acid onto a resin;
c) synthesis of the two peptide sequences on the grafted resin;
d) cyclisation.

The details of these steps are set out below.

In the protocols given below, the following abbreviations are used:
ACN: Acetonitrile; Boc: t-butyloxycarbonyl; DAC: 7-diethylaminocoumarin-3-carboxylic acid; DCM: dichloromethane; DIEA: N,N'-diisopropyldiethylamine; DMF: N,N-dimethylformamide; ESMS: electrospray mass spectrometry; Et$_2$O: diisopropylether; Fmoc: 9-fluorenylmethoxycarbonyl; HBTU: N-[1H-benzotriazol-1-yl)dimethylamino)methylene]-N-methylmethanaminium hexafluorophosphate N-oxide; HOBt: N-hydroxybenzotriazole; MC: 7-methoxycoumarin-3-carboxylic acid; AMPA: 4-aminophenylmercuric acetate; PyBOP: benzotriazol-1-yl-oxytris-pyrrolidonophosphonium; TA: ambient temperature; TFA: trifluoroacetic acid; THF: tetrahydrofuran; TIS: triisopropylsilane; TRIS: tris(hydroxymethyl)aminomethane.

All the chemical products and solvents are of analytical quality and were purchased from Sigma. The 2-chloro chlorotrityl resin, PyBOP and all the amino acids (Nα-protected by Fmoc) were purchased from Advanced Chemtech.

All the chemical reactions were performed under N$_2$ with anhydrous solvents. DMF is dried over CaH$_2$ under reflux overnight, and distilled. DCM was distilled before use.

The UV/visible spectra were recorded on Hitachi spectrophotometer equipment, model U-2010. The fluorescence spectra were conducted on PTI and Jobin-Yvon JY3 spectrofluorimetry apparatus with sample holder thermostated at 37° C. Peptide synthesis in solid phase was performed on an Applied Biosystem 433A synthesizer. Purifications were carried out on reverse phase Shimadzu HPLC (controller: SLC-10 AVP, pumps: LC8A, UV/Visible detector: SPD-10 AVP [wavelengths 214, 267 and 254 nm] and C18 Satisfaction column RP18AB 5 μm 250*4.6 mm). The solvent system used for elution was (A) a 0.1% aqueous solution of TFA and (B) a 70% aqueous solution of ACN.

a) Synthesis of Fmoc-Lys-OAllyl

Fmoc-Lys-OAllyl meets the following formula:

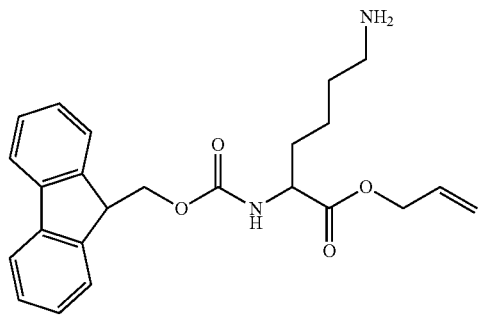 [SMILES: C=CCOC(=O)C(CCCCN)NC(=O)OCC1c2ccccc2-c2ccccc21]

It is prepared using the following reaction scheme:

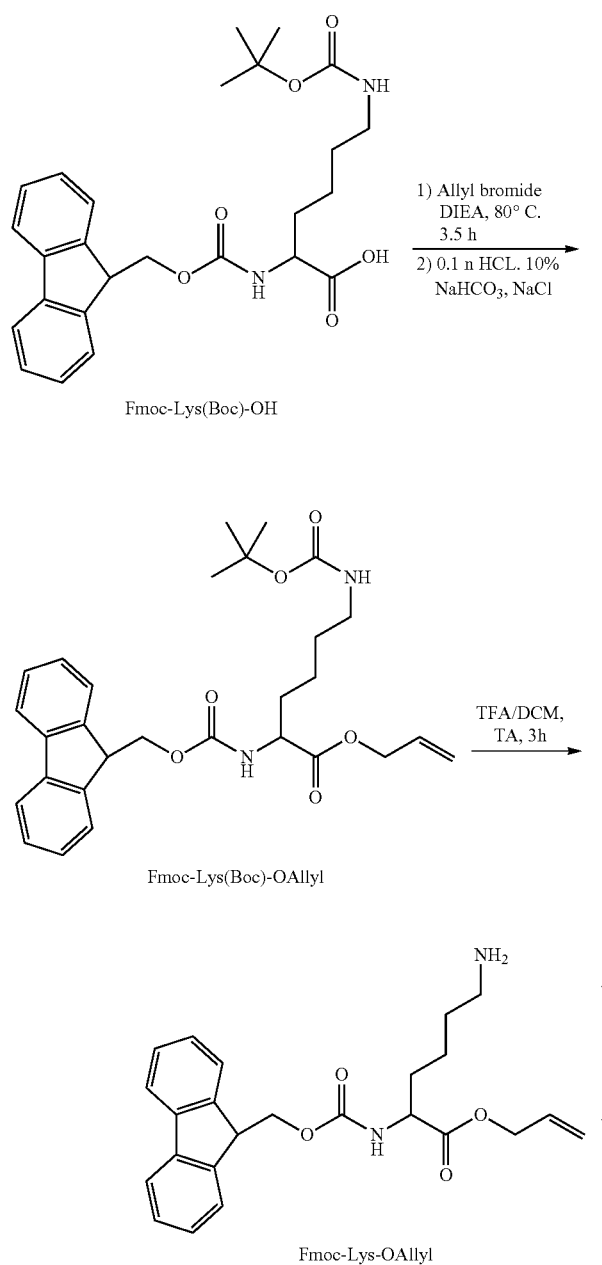

b) Grafting of Fmoc-Lys(Boc)-OAllyl onto a Resin and of a Lys(MC) Probe

The reaction scheme is the following:

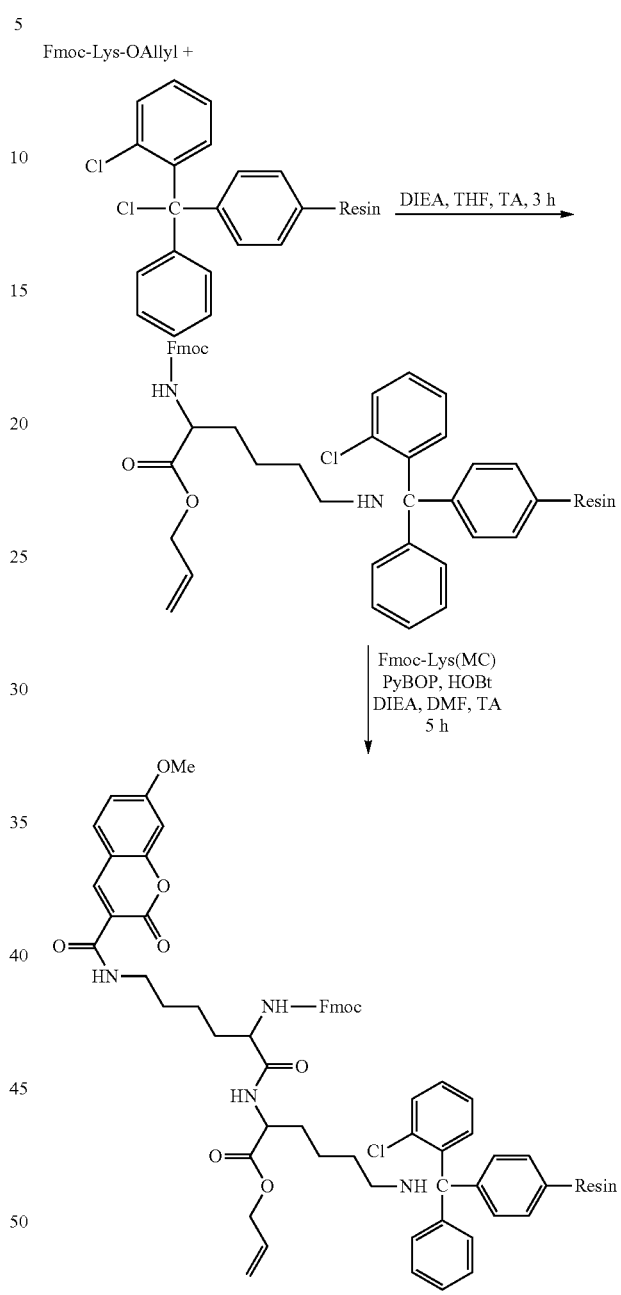

To a solution of Fmoc-Lys(Boc)-OH (2 g, 4.3 mmol) and allyl bromide (10 mL, 118.2 mmol) the addition is made of 1.45 mL DIEA (8.5 mmol). After agitation at 80° C. for 3.5 heures, the solution is diluted with 200 mL ethyl acetate then washed in 0.1 N HCl (3*100 mL), 10% NaHCO$_3$ (3*100 mL) and NaCl saturated solution (3*100 mL) then dried over MgSO$_4$. After evaporation under reduced pressure, 1.9 g Fmoc-Lys(Boc)-OAllyl (3.87 mmol, 90%) are obtained in the form of a white powder.

The Fmoc-Lys(Boc)-OAllyl (1.9 g, 3.87 mmol) is dissolved in a TFA/DCM mixture (70 mL, 1:1). The solution is agitated at ambient temperature for 3 hours. After concentrating the solution, washings with ether and successive evaporations 1.45 g Fmoc-Lys-OAllyl (3.56 mmol, 92%) are retrieved in the form of a white powder.

The Fmoc-Lys(Boc)-OAllyl (1.81 g, 4.43 mmol) is dissolved in anhydrous THF (2 mL), and DIEA (734 µL, 4.23 mmol) is added. After 10 minutes agitation at ambient temperature, 570 mg of 2-chlorotrityl resin are added. The mixture is agitated for 5 hours at ambient temperature. The resin is then filtered and washed with DMF (20 mL), a DCM/methanol/DIEA mixture (17:2:1) (2*20 mL), DMF (10 mL) and DCM (20 mL). The substitution rate of this new resin was determined at 0.4 mmol/g via UV measurement of the dibenzofulvene complex after treating with piperidine. Initially, the Fmoc-Lys-OAllyl-chlorotrityl resin (300 mg, 0.4 mmol/g) was deprotected through release of the Fmoc group, by placing said resin in contact with a 20% mixture of piperidine in DMF at ambient temperature for 3 hours. The presence of free primary amine was verified using the Kaiser test. This resin is left to react with Fmoc-Lys(MC)—OH (228 mg, 0.4 mmol) in the presence of PyBOP (173 mg, 0.392 mmol), HOBt (54 mg, 0.4 mmol) and DIEA (100 µL, 0.8 mmol) in DMF (5 mL) for 6 hours at ambient temperature. The resin is then filtered and washed with DMF, DCM and methanol. 270 mg of Fmoc-Lys(MC)-Lys-OAllyl-chlorotrityl resin are retrieved. The substitution rate of this new resin was determined at 0.38 mmol/g by UV measurement of the dibenzofulvene complex after treating with piperidine. The amine functions which did not react were acetylated in the presence of succiminide ester acetylate (25.12 mg, 0.16 mmol), piperidine (12 mg, 0.16 mmol) in DMF (5 mL) for 40 minutes at ambient temperature.

c) Peptide Synthesis

The reaction scheme is the following:

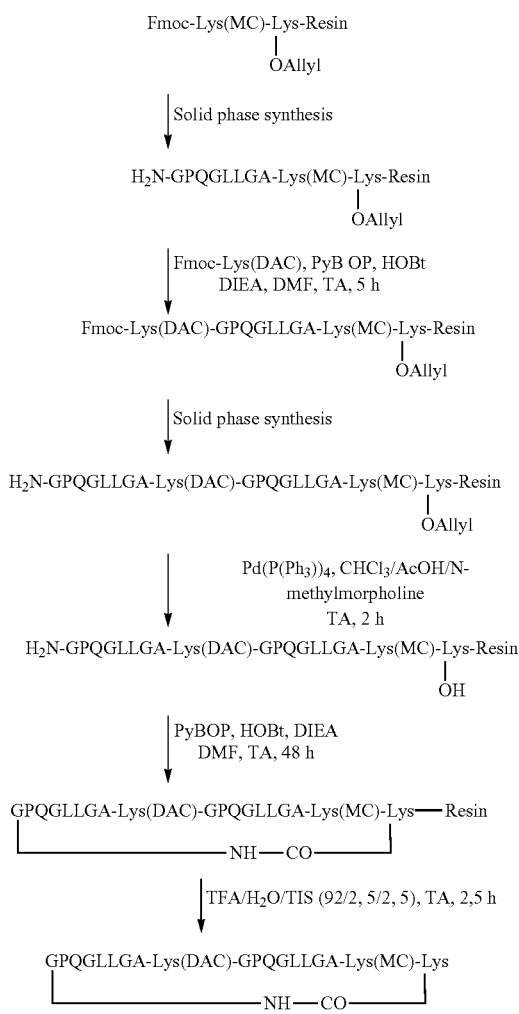

the codes G, P, Q, L and A respectively corresponding to the amino acids glycine, proline, glutamine, leucine, alanine.

The Fmoc-Lys(MC)-Lys-OAllyl-chlorotrityl resin is added to the synthesizer reactor. The amino acids (Gly, Pro, Gln(Trt), Leu and Ala) Nα-protected by a Fmoc group are added in excess (10 times). The coupling steps are performed in the presence of HBTU, HOBt and DIEA, after which the following peptide GPQGLLGA- is obtained, A being bonded to Lys(MC). After hours, 370 mg peptide bonded to the resin are obtained.

The Fmoc-Lys(DAC)—OH (190 mg, 0.3 mmol) is coupled, outside the synthesizer reactor, with the peptide-on-resin in the presence of PyBOP (153 mg, 0.3 mmol), HOBt (40.53 mg, 0.3 mmol) and DIEA (99.1 µL, 0.6 mmol) in DMF (5 mL) for 5 hours at ambient temperature. The resin is then filtered and washed as previously. 401 mg are collected. The substitution rate is evaluated at 0.25 mmol/g. The amine functions which do not react are acetylated following the same procedure as described above.

The peptide-on-resin is again added to the automatic peptide synthesizer reactor and the same sequence of amino acids as previously is synthesized following after the first. 530 mg are recovered.

d) Cyclisation

The resin is dried under a high vacuum for 4 hours then placed under argon. Pd(P(Ph$_3$))$_4$ (346.6, mg, 0.3 mmol) is dissolved in a chloroform/acetic acid/N-methylmorpholine mixture (37:2:1, 8 mL) under a stream of argon. This solution is then contacted with the resin and the resulting mixture is agitated occasionally at ambient temperature for 2 hours. The resin is then filtered, washed with a 0.5% DIEA solution in DMF (2*10 mL) then with a sodium diethyldithiocarbamate solution (0.5% w/w) in DMF, to remove the catalyst.

After Fmoc cleavage, the resin is washed with HOBt (1M) in DMF. To conduct cyclisation between the N and C terminal ends, 260 mg of PyBOP (0.5 mmol), mg HOBt (0.51 mmol) and 180 µL DIEA (1 mmol) are added to 10 mL N-methylpyrrolidone. The solution is agitated for 48 hours at ambient temperature after which the resin is washed with 30 mL DMF, DCM and methanol.

The resin is then suspended in a TFA/H$_2$O/TIS solution (95:2.5:2.5). After 3 hours at ambient temperature, the resin is filtered, washed with TFA (2*1 mL) and DCM (10 mL). The filtrate is partly evaporated under reduced pressure then immersed in cold ether.

After 12 hours at −20° C., the precipitate is filtered and washed to obtain 170 mg of raw product. After semi-preparative HPLC purification, 92.1 mg of peptide were obtained. The structure of the peptide was verified by ESMS.

The cyclic peptide obtained in this example meets the following formula:

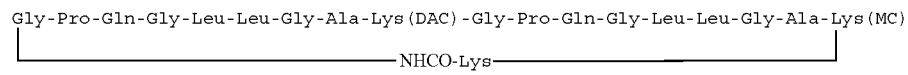

Enzymatic assays were conducted in a buffer solution containing 0.1 M TRIS, 0.1 M NaCl and 10 mM $CaCl_2$ at a pH of 7.6.

25 μL of commercial MMP-9 (90% zymogenous form) are activated with a solution of AMPA (1 mM) in the buffer solution at 37° C. for 4 hours. Commercial MMP-1 is already in activated form. A stock solution of cyclic peptide prepared according to the protocol set forth above is prepared with a buffer solution such as defined above to a final concentration of 90 μM. The solution of final concentration 90 μM was used as starting solution to carry out different dilutions so as to obtain 4 solutions of cyclic peptide/buffer, each having a concentration of 10, 5, 1 and 0.5 μM.

All the assays are conducted in a final reaction volume of 2 mL with 1 nM active MMP-1 or 2 nM AMPA-activated MMP-9.

Figure 1:
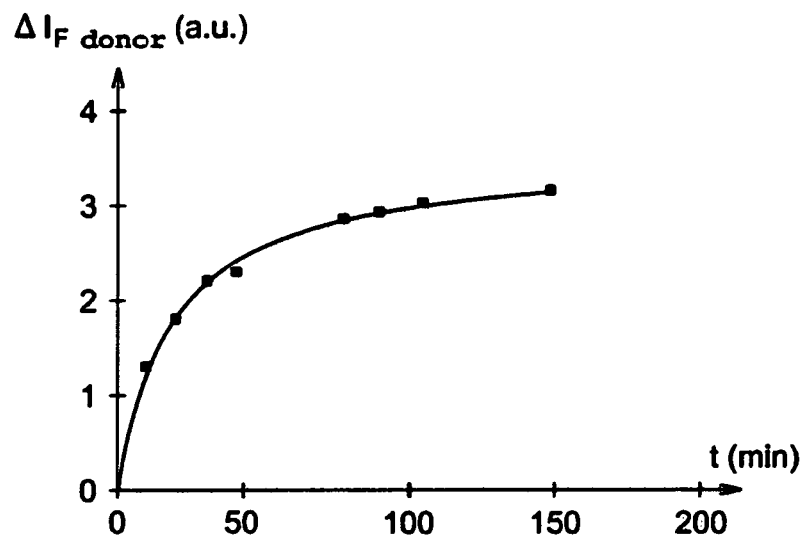

After adding the enzyme, the initial hydrolysis rate is determined by the variation over time of fluorescence intensity at 403 nm (at an excitation wavelength of 340 nm). For each concentration of assayed peptide concentration, a curve was plotted representing the variation in fluorescence intensity of the donor group $\Delta I_F$ (in a.u) as a function of time t (in min), as is illustrated FIG. 1 (for a cyclic peptide concentration of 10, 5, 1 and 0.5 μM).

From the following equation:

$$\text{Fluorescence}(t) = \text{fluorescence}_{max}(1-\exp(-k_{obs}t))$$

the first-order constant was able to be determined. Calculation of the second-order constant (called specificity constant) $k_{cat}/K_m$ is obtained by means of the concentration of active enzyme E used as per the equation $k_{cat}/K_m = k_{obs}/[E_0]$. The $k_{cat}/K_m$ of the peptide is evaluated at 319120 $s^{-1} \cdot M^{-1}$, a very high value compared with the best substrates of MMP-1 described in the literature, which evidences the very high specificity of the cyclic peptide prepared according to the invention for MMP-1.

Using the initial velocities of the different assays, the double reciprocal graph $(1/Vi)=f(1/[\text{cyclic peptide}])$ shown FIG. 2 allowed determination of the $K_m$ of the cyclic peptide, which totals 3.8 μM. This value is lower than the value obtained with the best MMP-1 substrates described in the literature, which evidences the excellent affinity of the cyclic peptide prepared according to the invention for MMP-1.

The cyclic peptide of the invention was also assayed in the presence of 2 nM of active MMP-9. No variation in the fluorescence intensity of the donor group was able to be measured over time. This cyclic peptide is not therefore a substrate of MMP-9, which indicates the selectivity of this cyclic peptide. This cyclic peptide also exhibits very high selectivity and and strong affinity for MMP-1.

The invention claimed is:

1. A cyclic peptide for quantifying the enzymatic activity of an MMP protease enzyme selected from the group consisting of MMP-1, MMP-2, MMP-3, MMP-5, MMP-7, MMP-8, MMP-9, MMP-10, MMP-11, MMP-12, MMP-13, MMP-14, MMP-15, MMP-16, MMP-17, MMP-19, MMP-23, MMP-25 and MMP-26, wherein said cyclic peptide comprises:

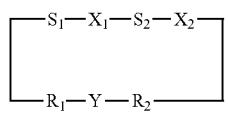

, wherein:

$S_1$ is a first target peptide sequence of an MMP protease enzyme $E_1$, wherein $S_1$ is capable of being recognized and cleaved by said MMP protease enzyme $E_1$;

$S_2$ is a second target peptide sequence of an MMP protease enzyme $E_2$, wherein $S_2$ is capable of being recognized and cleaved by said MMP protease enzyme $E_2$ and wherein $S_1$ and $S_2$ are the same or different;

$E_1$ and $E_2$ correspond to the same MMP protease enzyme;

$X_1$ is a probe carrying a fluorescent donor group and $X_2$ is a probe carrying a fluorescent or non-fluorescent acceptor group;

$R_1$ and $R_2$ independently correspond to a simple bond, an amino acid residue or a peptide sequence; and Y is a —CONH— or —NHCO— group;

wherein the MMP protease enzyme is selected from the group consisting of MMP-1, MMP-2, MMP-3, MMP-5, MMP-7, MMP-8, MMP-9, MMP-10, MMP-11, MMP-12, MMP-13, MMP-14, MMP-15, MMP-16, MMP-17, MMP-19, MMP-23, MMP-25 and MMP-26; and wherein the MMP protease enzyme is MMP-1, and wherein at least one of said first sequence $S_1$ or the second sequence $S_2$, corresponds to at least one of the following sequences:

SEQ. 1:
-Gly-Pro-Gln-Gly-Leu-Leu-Gly-Ala-

SEQ. 2:
-Ala-Pro-Gln-Gly-Ile-Ala-Gly-Gln-

SEQ. 3:
-Gly-Pro-Gln-Gly-Leu-Ala-Gly-Gln-

SEQ. 4:
-Gly-Pro-Leu-Gly-Ile-Ala-Gly-Ile-

SEQ. 5:
-Gly-Pro-Glu-Gly-Leu-Arg-Val-Gly-

SEQ. 6:
-Tyr-Glu-Ala-Gly-Leu-Gly-Val-Val-

SEQ. 7:
-Ala-Gly-Leu-Gly-Val-Val-Glu-Arg-

SEQ. 8:
-Ala-Gly-Leu-Gly-Ile-Ser-Ser-Thr-

SEQ. 9:
-Gly-Ala-Met-Phe-Leu-Glu-Ala-Ile-

SEQ. 10:
-Ile-Pro-Glu-Asn-Phe-Phe-Gly-Val-

SEQ. 11:
-Thr-Glu-Gly-Glu-Ala-Arg-Gly-Ser-

SEQ. 12:
-Arg-Ala-Ile-His-Ile-Gln-Ala-Glu-

SEQ. 13:
-Leu-Arg-Ala-Tyr-Leu-Leu-Pro-Ala-

SEQ. 14:
-Gly-Pro-Leu-Gly-Met-Arg-Gly-Leu-

SEQ. 15:
-Pro-Gln-Gly-Leu-Glu-Ala-Lys-

SEQ. 16:
-Pro-Leu-Gly-Leu-Trp-Ala-D-Arg-

SEQ. 17:
-Pro-Leu-Ala-Leu-Trp-Ala-Arg-

SEQ. 18:
-Pro-Cha-Abu-Cys(Me)-His-Ala-

SEQ. 19:
-Pro-Cha-Gly-Cys(Me)-His-Ala-

SEQ. 20:
-Pro-Cha-Gly-Cys(Me)-His-Ala-

SEQ. 21:
-Pro-Leu-Gly-Leu-Dpa-Ala-Arg-

SEQ. 22:
-Pro-Leu-Gly-[2-mercapto-4-methyl-pentanoyl]-Leu-Gl

SEQ. 23:
-Pro-Leu-Gly-Cys(Me)-His-Ala-D-Arg-

SEQ. 24:
-Arg-Pro-Leu-Ala-Leu-Trp-Arg-

SEQ. 25:
-Pro-Cha-Gly-Nva-His-Ala-

SEQ. 26:
-Arg-Pro-Lys-Pro-Tyr-Ala-Nva-Trp-Metwherein the MMP protease enzyme is MMP-2, and wherein at least one of said first sequence $S_1$ or the second sequence $S_2$, corresponds to at least one of the following sequences:

SEQ. 10:
-Ile-Pro-Glu-Asn-Phe-Phe-Gly-Val-

SEQ. 12:
-Arg-Ala-Ile-His-Ile-Gln-Ala-Glu-

SEQ. 13:
-Leu-Arg-Ala-Tyr-Leu-Leu-Pro-Ala-

SEQ. 16:
-Pro-Leu-Gly-Leu-Trp-Ala-D-Arg-

SEQ. 21:
-Pro-Leu-Gly-Leu-Dpa-Ala-Arg-

SEQ. 22:
-Pro-Leu-Gly-[2-mercapto-4-methyl-pentanoyl]-Leu-Gl

SEQ. 23:
-Pro-Leu-Gly-Cys(Me)-His-Ala-D-Arg-

SEQ. 24:
-Arg-Pro-Leu-Ala-Leu-Trp-Arg-

SEQ. 25:
-Pro-Cha-Gly-Nva-His-Ala-

SEQ. 26:
-Arg-Pro-Lys-Pro-Tyr-Ala-Nva-Trp-Met-

SEQ. 27:
Pro-Pro-Gly-Ala-Tyr-His-Gly-Ala-

SEQ. 28
-Gly-Pro-His-Leu-Leu-Val-Glu-Ala-

SEQ. 29:
-Pro-Gln-Gly-Leu-Glu-Ala-Lys-

SEQ. 30:
-Pro-Leu-Ala-Nva-Dpa-Ala-Arg-

SEQ. 31:
-Pro-Leu-Gly-Met-Trp-Ser-Arg-

SEQ. 32:
-Pro-Leu-Gly-SCH[CH$_2$CH(CH$_3$)$_2$]-CO-Leu-Gly-

SEQ. 33:
-Arg-Pro-Pro-Gly-Phe-Ser-Ala-Phewherein the MMP protease enzyme is MMP-3, and wherein at least one of said first sequence $S_1$ or the second sequence $S_2$, corresponds to at least one of the following sequences:

SEQ. 5:
-Gly-Pro-Glu-Gly-Leu-Arg-Val-Gly-

SEQ. 10:
-Ile-Pro-Glu-Asn-Phe-Phe-Gly-Val-

SEQ. 12:
-Arg-Ala-Ile-His-Ile-Gln-Ala-Glu-

SEQ. 13:
-Leu-Arg-Ala-Tyr-Leu-Leu-Pro-Ala-

SEQ. 15:
-Pro-Gln-Gly-Leu-Glu-Ala-Lys-

SEQ. 16:
-Pro-Leu-Gly-Leu-Trp-Ala-D-Arg-

SEQ. 20:
-Pro-Cha-Gly-Cys(Me)-His-Ala-

SEQ. 21:
-Pro-Leu-Gly-Leu-Dpa-Ala-Arg-

SEQ. 22:
-Pro-Leu-Gly-[2-mercapto-4-methyl-pentanoyl]-Leu-Gl

SEQ. 26:
-Arg-Pro-Lys-Pro-Tyr-Ala-Nva-Trp-Met-

SEQ. 28
-Gly-Pro-His-Leu-Leu-Val-Glu-Ala-

SEQ. 34:
-Arg-Val-Gly-Phe-Tyr-Glu-Ser-Asp-

SEQ. 35:
-Leu-Leu-Ser-Ala-Leu-Val-Glu-Thr-

SEQ. 36:
-Glu-Ala-Ile-Pro-Met-Ser-Ile-Pro-

SEQ. 37:
-Ile-Ala-Gly-Arg-Ser-Leu-Asn-Pro-

SEQ. 38:
-Lys-Pro-Gln-Gln-Phe-Phe-Gly-Leu-

SEQ. 39
-Asp-Val-Ala-Gln-Phe-Val-Leu-Thr-

SEQ. 40:
-Asp-Thr-Leu-Glu-Val-Met-Arg-Lys-

SEQ. 41:
-Asp-Val-Gly-His-Phe-Arg-Thr-Phe-

SEQ. 42:
-Asp-Ser-Gly-Gly-Phe-Met-Leu-Thr-

SEQ. 43:
-Arg-Val-Ala-Glu-Met-Arg-Gly-Glu-

SEQ. 44:
-Asp-Leu-Gly-Arg-Phe-Gln-Thr-Phe-

SEQ. 45:
-Pro-Phe-Ser-Pro-Leu-Val-Ala-Thr-

SEQ. 46:
-Ala-Pro-Gly-Asn-Ala-Ser-Glu-Ser-

SEQ. 47:
-Phe-Ser-Ser-Glu-Ser-Lys-Arg-Glu-

SEQ. 48:
-Pro-Pro-Glu-Glu-Leu-Lys-Phe-Gln-

SEQ. 49:
-Gly-Pro-Leu-Gly-Met-Arg-Gly-Leu-

SEQ. 50:
-Arg-Pro-Lys-Pro-Val-Glu-Nva-Trp-Arg-Glu-Ala-Lys-

SEQ. 51:
-Pro-Tyr-Ala-Tyr-Trp-Met-Arg-

SEQ. 52:
-Arg-Pro-Lys-Pro-Leu-Ala-Nva-Trpwherein the MMP protease enzyme is MMP-5, and wherein said first sequence $S_1$ or said second sequence $S_2$, corresponds to:

SEQ ID NO. 50:
-Arg-Pro-Lys-Pro-Val-Glu-Nva-Trp-Arg-Glu-Ala-Lys-
or wherein the MMP protease enzyme is MMP-7, and wherein at least one of said first sequence $S_1$ or the second sequence $S_2$, corresponds to at least one of the following sequences:

SEQ. 16:
-Pro-Leu-Gly-Leu-Trp-Ala-D-Arg-

SEQ. 17:
-Pro-Leu-Ala-Leu-Trp-Ala-Arg-

SEQ. 20:
-Pro-Cha-Gly-Cys(Me)-His-Ala-

SEQ. 21:
-Pro-Leu-Gly-Leu-Dpa-Ala-Arg-

SEQ. 22:
-Pro-Leu-Gly-[2-mercapto-4-methyl-pentanoyl]-Leu-Gl

SEQ. 24:
-Arg-Pro-Leu-Ala-Leu-Trp-Arg-

SEQ. 51:
-Pro-Tyr-Ala-Tyr-Trp-Met-Arg-

SEQ. 52:
-Arg-Pro-Lys-Pro-Leu-Ala-Nva-Trpwherein the MMP protease enzyme is MMP-8, and wherein at least one of said first sequence $S_1$ or the second sequence $S_2$, corresponds to at least one of the following sequences:

SEQ. 16:
-Pro-Leu-Gly-Leu-Trp-Ala-D-Arg-

SEQ. 17:
-Pro-Leu-Ala-Leu-Trp-Ala-Arg-

SEQ. 20:
-Pro-Cha-Gly-Cys(Me)-His-Ala-

SEQ. 21:
-Pro-Leu-Gly-Leu-Dpa-Ala-Arg-

SEQ. 22:
-Pro-Leu-Gly-[2-mercapto-4-methyl-pentanoyl]-Leu-Gl

SEQ. 23:
-Pro-Leu-Gly-Cys(Me)-His-Ala-D-Arg-

SEQ. 24:
-Arg-Pro-Leu-Ala-Leu-Trp-Arg-

SEQ. 25:
-Pro-Cha-Gly-Nva-His-Ala-

SEQ. 53:
-Pro-Leu-Ala-Tyr-Trp-Ala-Argwherein the MMP protease enzyme is MMP-9, and wherein at least one of said first sequence $S_1$ or the second sequence $S_2$, corresponds to at least one of the following sequences:

SEQ ID NO. 12:
-Arg-Ala-Ile-His-Ile-Gln-Ala-Glu-

SEQ ID NO. 14:
-Gly-Pro-Leu-Gly-Met-Arg-Gly-Leu-

SEQ ID NO. 15:
-Pro-Gln-Gly-Leu-Glu-Ala-Lys-

SEQ ID NO. 16:
-Pro-Leu-Gly-Leu-Trp-Ala-D-Arg-

SEQ ID NO. 19:
-Pro-Cha-Gly-Cys(Me)-His-Ala-

SEQ ID NO. 20:
-Pro-Cha-Gly-Cys(Me)-His-Ala-

SEQ ID NO. 21:
-Pro-Leu-Gly-Leu-Dpa-Ala-Arg-

SEQ ID NO. 22:
-Pro-Leu-Gly42-[2-mercapto-4-methyl-pentanoyl]-
Leu-Gly-

SEQ ID NO. 23:
-Pro-Leu-Gly-Cys(Me)-His-Ala-D-Arg

SEQ ID NO. 32:
-Pro-Leu-Gly-SCH[CH$_2$CH(CH$_3$)$_2$]-CO-Leu-Gly-

SEQ ID NO. 33:
-Arg-Pro-Pro-Gly-Phe-Ser-Ala-Phe-

SEQ ID NO. 50:
-Arg-Pro-Lys-Pro-Val-Glu-Nva-Trp-Arg-Glu-Ala-Lys-

SEQ ID NO. 54:
-Gly-Pro-Pro-Gly-Val-Val-Gly-Pro-

SEQ ID NO. 55:
-Gly-Pro-Pro-Gly-Leu-Arg-Gly-Glu-

SEQ ID NO. 56:
-Gly-Pro-Gly-Gly-Val-Val-Gly-Pro-

SEQ ID NO. 57:
-Ile-Pro-Gln-Asn-Phe-Phe-Gly-Val- or

SEQ ID NO. 58:
-Pro-Pro-Gly-Ala-Tyr-His-Gly-Ala- or wherein the MMP protease enzyme is MMP-10, and wherein at least one of said first sequence $S_1$ or the second sequence $S_2$, corresponds to at least one of the following sequences:

SEQ ID NO. 12: -Arg-Ala-Ile-His-Ile-Gln-Ala-Glu-

SEQ ID NO. 21: -Pro-Leu-Gly-Leu-Dpa-Ala-Arg- or

SEQ ID NO. 28: -Gly-Pro-His-Leu-Leu-Val-Glu-Ala- or wherein the MMP protease enzyme is MMP-11, and wherein at least one of said first sequence $S_1$ or the second sequence $S_2$, corresponds to at least one of the following sequences:

SEQ ID NO. 20:      -Pro-Cha-Gly-Cys(Me)-His-Ala- or

SEQ ID NO. 21:      -Pro-Leu-Gly-Leu-Dpa-Ala-Arg- or wherein the MMP protease enzyme is MMP-12, and wherein at least one of said first sequence $S_1$ or the second sequence $S_2$, corresponds to at least one of the following sequences:

SEQ ID NO. 17:
-Pro-Leu-Ala-Leu-Trp-Ala-Arg-

SEQ ID NO. 20:
-Pro-Cha-Gly-Cys(Me)-His-Ala-

SEQ ID NO. 21:
-Pro-Leu-Gly-Leu-Dpa-Ala-Arg-

SEQ ID NO. 22:
-Pro-Leu-Gly-[2-mercapto-4-methyl-pentanoyl]-Leu-
Gly-

SEQ ID NO. 23:
-Pro-Leu-Gly-Cys(Me)-His-Ala-D-Arg-

SEQ ID NO. 24:
-Arg-Pro-Leu-Ala-Leu-Trp-Arg-

SEQ ID NO. 25:
-Pro-Cha-Gly-Nva-His-Ala-

SEQ ID NO. 26:
-Arg-Pro-Lys-Pro-Tyr-Ala-Nva-Trp-Met-

SEQ ID NO. 27:
Pro-Pro-Gly-Ala-Tyr-His-Gly-Ala-

SEQ ID NO. 50:
-Arg-Pro-Lys-Pro-Val-Glu-Nva-Trp-Arg-

SEQ ID NO. 51:
-Pro-Tyr-Ala-Tyr-Trp-Met-Arg-

SEQ ID NO. 52:
-Arg-Pro-Lys-Pro-Leu-Ala-Nva-Trp- or

SEQ ID NO. 59:
-Arg-Pro-Lys-Pro-Gln-Gln-Phe-Trp- or wherein the MMP protease enzyme is MMP-13, and wherein at least one of said first sequence $S_1$ or the second sequence $S_2$, corresponds to at least one of the following sequences:

SEQ ID NO. 16:
-Pro-Leu-Gly-Leu-Trp-Ala-D-Arg-

SEQ ID NO. 17:
-Pro-Leu-Ala-Leu-Trp-Ala-Arg-

SEQ ID NO. 20:
-Pro-Cha-Gly-Cys(Me)-His-Ala-

SEQ ID NO. 21:
-Pro-Leu-Gly-Leu-Dpa-Ala-Arg-

SEQ ID NO. 22:
-Pro-Leu-Gly-[2-mercapto-4-methyl-pentanoyl]-Leu-
Gly-

SEQ ID NO. 23:
-Pro-Leu-Gly-Cys(Me)-His-Ala-D-Arg-

SEQ ID NO. 24:
-Arg-Pro-Leu-Ala-Leu-Trp-Arg-

SEQ ID NO. 25:
-Pro-Cha-Gly-Nva-His-Ala-

SEQ ID NO. 26:
-Arg-Pro-Lys-Pro-Tyr-Ala-Nva-Trp-Met-

SEQ ID NO. 31:
-Pro-Leu-Gly-Met-Trp-Ser-Arg-

SEQ ID NO. 49:
-Gly-Pro-Leu-Gly-Met-Arg-Gly-Leu-

SEQ ID NO. 50:
-Arg-Pro-Lys-Pro-Val-Glu-Nva-Trp-Arg-

SEQ ID NO. 51:
-Pro-Tyr-Ala-Tyr-Trp-Met-Arg-

SEQ ID NO. 52:
-Arg-Pro-Lys-Pro-Leu-Ala-Nva-Trp-

SEQ ID NO. 53:
-Pro-Leu-Ala-Tyr-Trp-Ala-Arg- or

SEQ ID NO. 59:
-Arg-Pro-Lys-Pro-Gln-Gln-Phe-Trp- or wherein the MMP protease enzyme is MMP-14, and wherein at least one of said first sequence S₁ or the second sequence S₂, corresponds to at least one of the following sequences:

```
SEQ ID NO. 20:
-Pro-Cha-Gly-Cys(Me)-His-Ala-

SEQ ID NO. 21:
-Pro-Leu-Gly-Leu-Dpa-Ala-Arg-

SEQ ID NO. 22:
-Pro-Leu-Gly-[2-mercapto-4-methyl-pentanoyl]-Leu-

Gly- or

SEQ ID NO. 60:
-Pro-Leu-Ala-Cys(p-OMeBz)-Trp-Ala-Arg- or
``` wherein the MMP protease enzyme is MMP-15, and wherein said first sequence S₁ or the second sequence S₂, corresponds to the sequence:

```
SEQ ID NO. 21:     -Pro-Leu-Gly-Leu-Dpa-Ala-Arg- or
``` wherein the MMP protease enzyme is MMP-16, and wherein said first sequence S₁ or the second sequence S₂, corresponds to the sequence:

```
SEQ ID NO. 21:     -Pro-Leu-Gly-Leu-Dpa-Ala-Arg- or
``` wherein the MMP protease enzyme is MMP-17, and wherein at least one of said first sequence S₁ or the second sequence S₂, corresponds to at least one of the following sequences:

```
SEQ ID NO. 21:
-Pro-Leu-Gly-Leu-Dpa-Ala-Arg-

SEQ ID NO. 22:
-Pro-Leu-Gly-[2-mercapto-4-methyl-pentanoyl]-Leu-

Gly- or
``` wherein the MMP protease enzyme is MMP-19, and wherein said first sequence S₁ or the second sequence S₂, corresponds to the sequence:

```
SEQ ID NO. 21:     -Pro-Leu-Gly-Leu-Dpa-Ala-Arg- or
``` wherein the MMP protease enzyme is MMP-23, and wherein at least one of said first sequence S₁ or the second sequence S₂, corresponds to the sequence:

```
SEQ ID NO. 21:     -Pro-Leu-Gly-Leu-Dpa-Ala-Arg- or
``` wherein the MMP protease enzyme is MMP-25, and wherein at least one of said first sequence S₁ or the second sequence S₂, corresponds to the sequence:

```
SEQ ID NO. 21:     -Pro-Leu-Gly-Leu-Dpa-Ala-Arg- or
``` wherein the MMP protease enzyme is MMP-26, and wherein at least one of said first sequence S₁ or the second sequence S₂, corresponds to the sequence:

```
SEQ ID NO. 16:     -Pro-Leu-Gly-Leu-Trp-Ala-D-Arg-.
```

2. The cyclic peptide according to claim 1, wherein the donor group carried by the X₁ probe and the acceptor group carried by the X₂ probe comprise an aromatic nucleus.

3. The cyclic peptide according to claim 2, wherein the donor group carried by the X₁ probe and the acceptor group carried by the X₂ probe comprise an aromatic nucleus and wherein said aromatic nucleus is selected from the group consisting of a benzene, anthracene and coumarin nucleus.

4. The cyclic peptide according to claim 1, wherein the donor group carried by the X₁ probe and the acceptor group carried by the X₂ probe are selected from the group of pairs consisting of: Tryptophan/2,4-dinitrophenyl; o-aminobenzoic acid/2,4-dinitrophenyl; (7-methoxycoumarin-4-yl)-acetyl/2,4-dinitrophenyl; (7-methoxycoumarin-4-yl)-acetyl/N-3-(2,4-dinitrophenyl)-L-2,3-diaminopropyl; Tryptophan/Dansyl; N-methylanthranoyl/2,4-dinitrophenyl; 6,7-dimethoxycoumarin-4-yl-acetyl/6-N-(7-nitrobenz-2-oxa-1,3-diazol-4-yl)aminohexanoic acid; 5-(2'-aminomethyl)naphtalene sulphonic acid/4-(4'-dimethylaminophenylaza)benzoic acid; and ethoxycoumarin-3-carboxylic acid/7-diethylaminocoumarin-3-carboxylic acid.

5. The cyclic peptide according to claim 1, wherein the donor group carried by the X₁ probe and the acceptor group carried by the X₂ probe comprise a coumarin nucleus.

6. The cyclic peptide according to claim 1, wherein the donor group carried by the X₁ probe and the acceptor group carried by the X₂ probe respectively correspond to the following formulas:

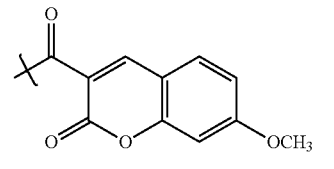

MC

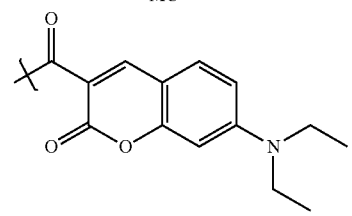

DAC

7. The cyclic peptide according to claim 1, wherein the probes X₁ and X₂ respectively meet the following formulas:

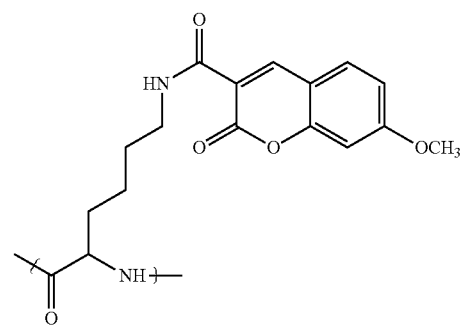

-continued

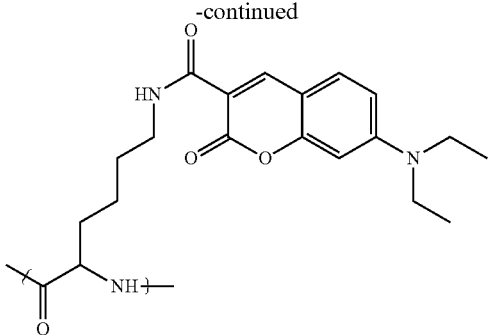

8. The cyclic peptide of claim 1, the peptide sequences $S_1$ and $S_2$ comprise the formula:

SEQ ID NO. 1:   -Gly-Pro-Gln-Gly-Leu-Leu-Gly-Ala-.

9. The cyclic peptide of claim 8, comprising the formula:
$R_1$, Y, $X_1$, $X_2$, and $R_2$ meeting the same definition as the definition given in claim 1.

10. The cyclic peptide of claim 9, wherein $R_1$ is a simple bond, $R_2$ is Lys, $X_1$ is Lys(DAC), and $X_2$ is Lys(MC).

11. A reagent comprising at least one cyclic peptide of claim 1.

12. A kit comprising:
a first compartment comprising at least one cyclic peptide of claim 1; and
a second compartment comprising a buffer solution.

* * * * *